United States Patent [19]

Rowe

[11] Patent Number: 5,279,937
[45] Date of Patent: Jan. 18, 1994

[54] USE OF MACROGLOBULINS TO IMPROVE THE SIGNAL-TO-BACKGROUND RATIO IN AFFINITY BINDING ASSAYS

[75] Inventor: Gerald E. Rowe, Ontario, Canada

[73] Assignee: DeTechnology Canada, Peterborough, Canada

[21] Appl. No.: 876,784

[22] Filed: Apr. 30, 1992

[51] Int. Cl.$^5$ .................... C12Q 1/68; C12Q 1/37; G01N 33/535; G01N 33/537

[52] U.S. Cl. ........................ 435/6; 435/7.92; 435/7.93; 435/23; 435/971; 436/538

[58] Field of Search .............. 435/6, 7.1, 7.9, 7.91, 435/7.92, 23, 962, 963; 436/538, 971

[56] References Cited

U.S. PATENT DOCUMENTS

| | | | |
|---|---|---|---|
| 3,817,837 | 6/1974 | Rubenstein | 195/103.5 R |
| 3,935,074 | 1/1976 | Rubenstein | 435/7.9 |
| 3,996,345 | 12/1976 | Ullman et al. | 436/537 |
| 4,193,983 | 3/1980 | Ullman | 429/12 |
| 4,208,479 | 6/1980 | Zuk et al. | 435/7.9 |
| 4,233,401 | 11/1980 | Yoshida | 435/7.8 |
| 4,256,834 | 3/1981 | Zuk et al. | 435/7.72 |
| 4,281,061 | 7/1981 | Zuk et al. | 435/7.9 |
| 4,341,866 | 7/1982 | Yoshida | 435/7.9 |
| 4,430,263 | 2/1984 | March et al. | 530/300 |
| 4,442,218 | 4/1984 | Amos et al. | 436/525 |
| 4,463,090 | 7/1984 | Harris | 435/7.7 |
| 4,582,792 | 4/1986 | Kasahara et al. | 435/7.71 |
| 4,598,042 | 7/1986 | Self | 435/7.91 |
| 4,607,010 | 8/1986 | Siddiqui et al. | 435/23 |
| 4,640,898 | 2/1987 | Halfman | 436/546 |
| 4,649,105 | 3/1987 | Kasahara et al. | 435/5 |
| 4,668,630 | 5/1987 | Louderback | 435/184 |
| 4,699,876 | 10/1987 | Libeskind | 435/5 |
| 4,743,535 | 5/1988 | Carrico | 435/6 |
| 4,745,054 | 5/1988 | Rabin et al. | 435/6 |
| 4,772,548 | 9/1988 | Stavrianopoulos | 435/5 |
| 4,785,080 | 11/1988 | Farina et al. | 530/402 |
| 4,789,630 | 12/1988 | Bloch et al. | 435/25 |
| 4,791,055 | 12/1988 | Boguslaski et al. | 435/7.7 |
| 4,810,631 | 3/1989 | Perlman et al. | 435/7.1 |
| 4,810,635 | 3/1989 | Ledden et al. | 435/7.7 |
| 4,820,630 | 4/1989 | Taub | 435/5 |
| 4,828,981 | 5/1989 | Maggio | 435/7.22 |
| 4,835,099 | 5/1989 | Mize et al. | 435/7.91 |
| 4,837,395 | 6/1989 | Leeder et al. | 435/7.8 |
| 4,843,010 | 6/1989 | Nowinski et al. | 435/2.7 |
| 4,868,106 | 9/1989 | Ito et al. | 433/7.7 |
| 4,869,875 | 9/1989 | Skov et al. | 422/58 |
| 4,894,326 | 1/1990 | Matsuura et al. | 435/7.21 |
| 4,904,583 | 2/1990 | Mapes et al. | 435/7.92 |
| 4,904,596 | 2/1990 | Hakomori | 435/240.27 |
| 4,960,693 | 10/1990 | Siddiqui et al. | 435/7.7 |
| 4,962,024 | 10/1990 | Schulte | 435/14 |
| 4,966,856 | 10/1990 | Ito et al. | 436/170 |
| 4,970,152 | 11/1990 | Ashida et al. | 435/19 |
| 5,006,462 | 4/1991 | Gattaz | 435/7.4 |
| 5,006,473 | 4/1991 | Bauma et al. | 536/516 |
| 5,035,995 | 7/1991 | Taguchi et al. | 435/4 |
| 5,057,430 | 10/1991 | Newman | 435/288 |

OTHER PUBLICATIONS

McMurray et al Biochemistry 25 #8 (1986) 2298-2301.

Barrett, A. J. (1981), Meth. Enzymol. 80,737-754. "$\alpha_2$--Macroglobulin".

Chan, D. W. (1987), pp. 1-23, in D. W. Chan and M. T. Perlstein (Eds.), Immunoassay: A practical guide, Academic Press, Orlando, Fla. "General Principle of Immunoassay".

Gould, B. J., and Marks, V. (1988), pp. 3-26, in T. T. Ngo (Ed.), Nonisotopic Immunoassay, Plenum Press, New York, N.Y. "Recent Developments in Enzyme Immunoassays".

Ishikawa, E., Hashida, S., and Kohno, T. (1991), Mol. Cell. Probes 5, 81-95. "Development of ultrasensitive enzyme immunoassay reviewed with emphasis on factors which limit the sensitivity".

(List continued on next page.)

Primary Examiner—Esther L. Kepplinger
Assistant Examiner—Nancy J. Parsons
Attorney, Agent, or Firm—Iver P. Cooper

[57] ABSTRACT

A macroglobulin is used to improve the signal-to-background ratio in an affinity binding assay employing a proteinase (or precursor) as a label. The macroglobulin entraps unbound labeled reagent, thereby reducing its signal generating activity, relative to that of the affinity complex.

23 Claims, No Drawings

OTHER PUBLICATIONS

Kazanskaya, N. F., Aisina, R. B., and Berezin, I. V. (1983), Enzyme Microbial Technol. 5, 209–214. "Autocatalytic Enzyme System for Amplification of Light Signals".

Kwoh, D. Y., and Kwoh, T. J. (1990), Am. Biotechnol. Lab., Oct. 1990, 14–25. "Target amplification systems in nucleic acid-based diagnostic approaches".

Laskowski, M., Jr., and Kato, I. (1980), Ann. Rev. Biochem. 49, 593–626. "Protein Inhibitors of Proteinases".

Mayer, M., Khassis, S., and Shafrir, E. (1974), Anal. Biochem. 58, 25–29. "Determination of Trypsin by its Accelerating Effect on the Onset of Trypsinogen Activation".

Moss, D. W., Henderson, A. R., and Kachmar, J. F. (1987), pp. 346–421, in N. W. Tietz (Ed.) Fundamentals of Clinical Chemistry, 3rd ed., W. B. Saunders Co., Philadelphia, Pa. "Analytes, Methods, Pathophysiology, and Interpretation".

Ngo, T. T. (1985), pp. 3–32, in T. T. Ngo and H. M. Lenhoff (Eds.), Enzyme-mediated Immunoassay, Plenum Press, New York, N.Y. "Enzyme Mediated Immunoassay: An Overview".

Starkey, P. M., and Barrett, A. J. (1977), pp. 663–696, in A. J. Barrett (Ed.), Proteinases in Mammaliam Cells and Tissues, North–Holland, Amsterdam. "$\alpha_2$-Macroglobulin, a physiological regulator of proteinase activity".

Travis, J., and Salvesen, G. S. (1983), Ann. Rev. Biochem. 52, 655–709. "Human Plasma Proteinase Inhibitors".

USE OF MACROGLOBULINS TO IMPROVE THE SIGNAL-TO-BACKGROUND RATIO IN AFFINITY BINDING ASSAYS

The present invention is described in part in Disclosure Document 284,639, filed Jun. 17, 1991, entitled "Molecular Background Reduction Providing Rapid Ultra-Sensitive Assays", and Disclosure Document 285,787, filed Jul. 2, 1991, entitled "Addendum to Molecular Background...". These documents are being retained by the U.S. Patent and Trademark Office as evidence of conception, pursuant to the Disclosure Document Program.

BACKGROUND OF THE INVENTION

1. Field of the Invention

This invention relates to affinity binding assays, such as immunoassays and nucleic acid hybridization assays, in which enzymes are used as labels and the presence or level of a substance is inferred from the enzymatic activity observed.

2. Description of the Background Art

Affinity Binding Assays. Measurement or detection of minute amounts of analytes, especially but not exclusively substances of biological origin, typically relies on processes of molecular recognition to achieve specificity. By molecular recognition is meant a highly specific interaction between two molecules, by virtue of which they bind to each other with high affinity The complex so formed is typically denoted as an "affinity complex"; and one of its members is often designated as a "ligand" of the other. This phenomenon forms the basis of the well known technique of affinity chromatography. Prominent illustrative examples of molecular recognition are antibody-antigen complex formation and hydridization of complementary nucleic acids (cf. Journal of Molecular Recognition for further examples).

Analytical protocols are typically classified as "homogeneous" or "heterogeneous". Heterogeneous assays are those in which at least one component of the affinity complex is necessarily immobilized on a surface during all or part of the analysis, i.e. such immobilization is methodologically functional. Conversely, homogeneous assays do not require immobilization of either member of the affinity complex, i.e. the analysis occurs substantially in solution.

For a homogeneous assay to be successful, there must be a difference between the signal produced by the labeled reagent in the free and in the bound state. Amos, U.S. Pat. No. 4,442,218 (1984) permits a binding reaction to take place within the pores of an insoluble porous monolith. The signal produced by the labeled species, once bound within the pore, is attenuated relative to the signal emitted by the free label species. Zuk, U.S. Pat. No. 4,256,834 employs three reagents: an insolubilized ligand, a labeled (e.g. fluorescein) anti-ligand, and an insolubilized anti-label (e.g., anti-fluorescein antibody bound to charcoal). When the first two reagents form an affinity complex, the third, the signal repressor, is obstructed from interacting with the label. Free labeled anti-ligand, however, is complexed by the anti-label and its signal production is inhibited. Zuk, U.S. Pat. No. 4,281,061, discloses an assay which features a labeled ligand, an antiligand, an anti(antiligand), and a polyvalent macromolecule which can modulate the signal produced by the labeled ligand. Ligand, antiligand, and anti(antiligand) bind to form a matrix which either encloses the macromolecule (resulting in enhanced interaction) or excludes it (resulting in diminished interaction). The macromolecule is typically an antibody. Carrico, U.S. Pat. No. 4,743,535 (1988) teaches use of an antibody which binds to double-stranded but not single stranded DNA in a nucleic acid hybridization assay. The antibody sterically interferes with signal generation by the affinity complex. Halfman, U.S. Pat. No. 4,640,898 forms micelles which can distinguish unbound labeled conjugate and the conjugate as part of an affinity complex. See also Rubenstein U.S. Pat. No. 3,817,837; Ullman, U.S. Pat. No. 3,996,345; Rubenstein, U.S. Pat. No. 3,935,074.

Homogeneous assays offer several advantages relative to heterogeneous assays, including the following:
  i) no immobilization step is required;
  ii) time-consuming and labour-intensive washing steps are unnecessary;
  iii) capable of performance in a simple, reusable container such as a test tube, by addition of reagents without liquid withdrawal;
  iv) more rapid analysis due to improved mass-transfer kinetics.

In spite of these advantages very few operational homogeneous assay systems have been developed to-date. An important advantage of the present invention is that it functions in either homogeneous or heterogeneous assay formats. Moreover homogeneous assays employing the invention complement existing technology which can only measure analytes that are small molecules (Chan, 1987).

Another functional distinction is between competitive and non-competitve assays. A competitive assay relies on at least one process of competition between labelled and unlabelled species (e.g. analyte, antibody, DNA probe, etc.) for binding to a complementary molecule through a process of molecular recognition. Conversely a non-competitive assay requires only binding of a labelled probe to the analyte by a molecular recognition process. Because of thermodynamic constraints competitive assays are typically about one thousand-fold less sensitive than non-competitive assays: "Thus, the detection limit of antigens by competitive immunoassay is at femtomole [$10^{-15}$ mol] or higher levels in most cases...The detection limit of antigens by non-competitive two-site enzyme immunoassay with appropriate techniques is at attomole [$10^{-18}$ mol] levels." (Ishikawa et al , 1991).

In spite of these recognized advantages of non-competitive, homogeneous assays, it appears that no such systems have been developed to the point of practical utility. Thus, "Although competitive assays were used in early EIA [enzyme immunoassay] there has subsequently been a progressive increase in the use of non-competitive or immunoenzymometric assays...These assays all use solid-phase reagent, either an antibody or antigen." (Gould and Marks, 1988). Similarly all of the homogeneous immunoassay methods described by Ngo (1985) are of the competitive type. A significant advantage of the present invention is its general applicability in a non-competitive, homogeneous assay format, thereby deriving most or all of the benefits described above.

Assay Sensitivity. Heretofore detection methods relying on molecular recognition processes have suffered from compromises between detection limit and analysis time. Thus, "...although the theoretical detectability of catalyst [sic] could be as low as a single molecule, practical considerations of time and the inevitability of backgrounds have limited the sensitivity of enzyme-based assays." (Bates, 1987). The detection limit of heterogeneous assays has always been constrained by a non-specific, "background" (zero analyte) signal. Although to some extent reducible, such background has not heretofore been susceptible to substantial elimination: "In two-site enzyme immunoassay for antigen, enzyme-labelled antibody non-specifically (non-immunologically and physically) adsorbs to antibody-coated solid phase to various extents. This is one of the major obstacles to improvement in sensitivity and various attempts have been made to reduce the non-specific binding." (Ishikawa et al., 1991). None of these previous attempts have met with unqualified success.

The various sources of background signal were described as follows by Pruslin et al. (1991): "The OD (absorbance) measurements obtained in an assay include, in addition to the values for the specific antibody/antigen reaction, summary values designated 'background'. That designation includes all contributions to the OD that are not attributable to the specific antibody/antigen reaction under test. Those non-specific contributions are demonstrable by including a set of test wells with serum (antibody) but with antigen omitted, and a set of wells with the series of antigen concentrations, but with serum omitted.

In the first instance, the revealed 'background' may be due to reactivity of antibodies, other than the test antibody, with antigenic moieties in the reagents or to non-reactive serum components that are detected by the enzyme-labeled probe, second antibody. For the second set of 'control' wells, those with serum omitted, the revealed 'background' may be due to impurities in the antigen solution with which the probe antibody is reactive or to adventitious deposits of the enzyme-labeled probe on the well surface."

Considerable efforts have been expended to minimize the background signal in immunoassays. Present methods employed to this end include rigorous washing with surfactants (Mohammad and Esen, 1989), application of protein solutions to block non-specific adsorption sites (Pruslin et al., 1991), and careful selection of solid-phase and solution-phase antibodies (Aoyagi et al., 1991). In spite of such measures background interference remains, and complex and not entirely unambiguous calculations to compensate for same are necessary (Pruslin et al., 1991).

In order to reduce the fundamental limitation of non-specific background signal interference several reversible capture or transfer methods have been developed. These methods are all characterized by at least one transfer of analytical markers, especially the analyte itself, between two surfaces, generally for the purpose of background reduction. Lejeune et al. (1990) detected about $1 \times 10^{-19}$ mol of human growth hormone in four hours using two immunoaffinity resins. Ishikawa et al. (1991) describe methods developed to "transfer the complex of analytes and labelled reactants from solid phase to solid phase without dissociation." These repetitive and labour intensive procedures permit the measurement of about $1 \times 10^{-21}$ mol (about 600 molecules) of antigen in 15 to 40 hours. Nevertheless, "One of the greatest obstacles limiting the sensitivity of non-competitive solid phase enzyme immunoassays is the non-specific binding of enzyme-labelled reactants to solid phase." (ibid.) Similar reversible capture methods using the avidin-biotin interaction were recently advocated for background reduction prior to polymerase chain reaction (PCR) amplification of DNA (Yolken et al., 1991).

Direct unamplified measurement of small amounts of specific nucleic acids or oligonucleotides suffers from the same compromise between detection limit and analysis time as found with present immunochemical methods. Molecular recognition of complementary DNA strands (hybridization) was used by Syvanen et al. (1986) to detect as few as $4 \times 10^5$ molecules of nucleic acid in 3 hours. Similarly, $6 \times 10^4$ molecules of viral DNA were detected in 4 hours by use of an oligonucleotide (i.e. nucleotide polymer) probe coupled to enzyme (Urdea et al., 1987). Such methods suffer from interference due to high background signal when applied to crude samples (Hames and Higgins, 1985). Thus Syvanen et al. (1986) could detect no fewer than $5 \times 10^5$ cells; and a detection limit of $2 \times 10^7$ bacterial cells in 4.5 to 5 hours was reported by Kennedy et al. (1989). The recognized limitations of direct methods of nucleic acid detection led to the development of various DNA amplification schemes.

Enzymatic Amplification of Signal. Another method used to increase sensitivity is enzymatic amplification of the initial signal. Direct (unamplified) immunochemical analysis faces fundamental limitations due to equilibrium, kinetic and mass transport constraints. Thus, "while improvement in sensitivity and detection limit might always be made in principle by choosing an antibody-antigen pair with higher affinity, this improvement is made at the expense of an increased response time." (Eddowes, 1987/88). Although about $3 \times 10^{-15}$ mol of substance per ml are detectable in less than one hour (Liabakk et al., 1990), detection of $7 \times 10^{-17}$ mol of substance requires 18 hours (Aoyagi et al., 1991). The practical limit for detection of Salmonella by direct immunochemical assay was recently reported as $10^3$ to $10^4$ cells/ml in 2 to 3 hours (Luk and Lindberg, 1991).

Enzymatically amplified immunoassays employing alkaline phosphatase combined with cofactor cycling have been reported to be capable of detecting $10^5$ molecules during long incubation times (Bates, 1989). More recently less than $10^{-19}$ mol (about $6 \times 10^4$ molecules) of substance have been detected in 2 hours, but ten thousand times this amount had to be present for detection within an hour (Durkee et al., 1990).

Several immunochemical detection or measurement methods employing enzymatic amplification are disclosed in the patent literature. Eur. Pat. No. 123,265 (Hall and Hargreaves, 1983) teaches that signal amplification can be achieved by covalent coupling of an analyte molecule to a zymogen such as trypsinogen. In U.S. Pat. No. 4,463,090 (Harris, 1984) signal amplification is obtained by a 3- or 4-stage enzyme cascade initiated by an enzyme or zymogen coupled to an immuno-reactive substance. This patent stipulates that it is necessary to use a different enzyme/zymogen pair at each amplification stage, thus limiting the amplification effect to a 3 or 4-stage geometric increase. In U.S. Pat. No. 4,598,042 (Self, 1981) it is disclosed that signal amplification can be achieved when the product of a primary enzyme, especially alkaline phosphatase, participates in a secondary enzyme cycle. U.S. Pat. No. 4,745,054 (Rabin et al., 1988) teaches that two inactive fragments can be combined to form an active enzyme which then activates a second enzyme leading to a detectable result. None of these enzyme cascade methods exploit the most effective type of amplification, namely an exponential increase with time.

Although heretofore not applied to amplification of enzymatic activity coupled to a substance capable of molecular recognition of an analyte, exponential amplification is well known in the biochemical literature. For example, trypsinogen (zymogen) formed in the pancreas of mammals is converted to trypsin by traces of trypsin or enteropeptidase in the intestine (Moss et al., 1987). This so-called "autocatalytic" process produces an exponential increase in the amount of enzyme (Pechère and Neurath, 1957). This principle has been used to measure low concentrations of trypsin after amplification by activation of trypsinogen (Mayer et al., 1974; Aisina et al., 1975; Kazanskaya et al., 1983).

Several strategies for ultra-sensitive detection of nucleic acids based on their exponential amplification have recently been reviewed (Kwoh and Kwoh, 1990). The polymerase chain reaction (PCR) amplification method has rapidly achieved wide acceptance in research applications in spite of its numerous limitations and disadvantages (Lizardi and Kramer, 1991). While PCR methodology has in principle a detection limit of a single oligonucleotide, it suffers from the heretofore universal problem of background interference, as well as from contamination by amplifiable DNA (Kwok and Higuchi, 1989). Furthermore the procedure requires several hours to achieve significant amplification using dedicated and sophisticated equipment. Although detection of 1 to 2 cells has been accomplished in a 5 to 7 hour period, complex manipulations are required for analysis of actual crude samples (Bej et al., 1990). Finally, since the amplification yield in each cycle varies unpredictably, PCR is not well suited for quantitative measurement of nucleic acid concentration (Lizardi and Kramer, 1991). Since PCR analyses for ribonucleic acid (RNA) simply add an initial RNA to DNA transcription step they suffer from all of the above disadvantages (Rose, 1990).

Q-beta amplification, another nucleic acid analysis method under development, has a detection limit of about 2,000 molecules of DNA, but also suffers from several disadvantages (Lizardi and Kramer, 1991). Specifically this technique requires repetitive, multi-step, mass-transfer limited operations to reduce the background signal level prior to amplification. Although amplification with Q-beta replicase is rapid, these multiple hybridization steps appear to impose a minimum analysis time of several hours. Furthermore, contamination and background interference are once again limitations: "A problem that remains to be solved in order to reach the theoretical detection limit of one molecule is the removal of the few hundred probe molecules that are carried along non-specifically with the probe-target complexes during washing, despite reversible target capture. These non-specifically bound probe molecules are also amplified, giving rise to a background signal". (ibid). Finally, as for the PCR technique, dedicated and sophisticated equipment is required.

Signal modulation or amplification is further described in Mize, U.S. Pat. No. 4,835,099, Mapes, U.S. Pat. No. 4,904,583, Schulte, U.S. Pat. No. 4,962,024, Boguslaski, U.S. Pat. No. 4,791,055, Faring, U.S. Pat. No. 4,785,080, and Perlman, U.S. Pat. No. 4,810,631.

Use of Enzyme Inhibitors in Affinity Binding Assays. Enzyme inhibitors have been used as binding reagents (see March, U.S. Pat. No. 4,430,264; Gattaz, U.S. Pat. No. 5,006,462; Newman, U.S. Pat. No. 5,057,430) and as labels (Kasahara, U.S. Pat. No. 4,582,792 and U.S. Pat. No. 4,649,105; Taguchi, U.S. Pat. No. 5,035,995; Bloch, U.S. Pat. No. 4,789,630; Hakomori, U.S. Pat. No. 4,904,596; Matsuura, U.S. Pat. No. 4,894,326; Skov, U.S. Pat. No. 4,869,875; Navinski, U.S. Pat. No. 4,843,010; Maggio, U.S. Pat. No. 4,828,981; Stavrianopoulos, U.S. Pat. No. 4,772,548). See also Bauma, U.S. Pat. No. 5,006,473. Several patents teach use of an enzyme inhibitor to selectively inhibit the activity of an enzyme label. See Ito, U.S. Pat. No. 4,966,856 and 4,868,106; Leeder, U.S. Pat. No. 4,837,395; Gedden, U.S. Pat. No. 4,810,635; Ullman, U.S. Pat. No. 4,913,983; Yoshida, U.S. Pat. No. 4,341,866.

Yoshida, U.S. Pat. No. 4,208,479 teaches an immunoassay which involves bringing together an analyte and a labeled receptor so as to form a complex which sterically inhibits the approach of a macromolecular modifier, which otherwise would physically or chemically interact with the label to reduce its signal production. Where the label was an enzyme the disclosed modifiers were principally anti-(enzyme) antibodies and certain small, organic, irreversible inhibitors. For example, for serine proteases, the preferred inhibitor was physostigmine. Similar inhibitor systems were set forth for use with fluorescent labels. The teachings of Yoshida, U.S. Pat. No. 4,233,401 and Yoshida, U.S. Pat. No. 4,341,866 are similar.

Louderback, U.S. Pat. No. 4,668,0630, teaches use of a reversible inhibitor to protect an enzyme (lactate hydrogenase).

Alpha2-Macroglobulin. Assays for alpha2-macroglobulin have been described, see Siddiqui, U.S. Pat. No. 4,607,010, but A2M has not previously seen service as a signal modulator in a binding assay. A2M is also mentioned in Silvestrini, U.S. Pat. No. 5,047,509; Lorier, U.S. Pat. No. 5,013,568; Harpel, U.S. Pat. No. 4,629,694; Teodorescu, U.S. Pat. No. 4,499,186; and Schrenk, U.S. Pat. No. 4,414,332 and U.S. Pat. No. 4,393,139.

SUMMARY OF THE INVENTION

The present invention relates to the use of a macroglobulin, a class of molecules having a unique relationship with certain proteinases, to modulate the signal produced by those proteinases when used as a label in a binding assay, with the signal varying depending on whether or not an affinity complex was formed. As a result, the invention may be used to detect or measure any substance which binds to another molecule through a process of molecular recognition. Such analytes include, but are not limited to, immuno-reactive substances (antigens), antibodies, nucleic acids (DNA, RNA), and substances binding to so-called molecular receptors.

Analyte in the sample is exposed to a probe reagent possessing proteolytic activity in addition to the ability to bind effectively irreversibly to the analyte by a process of molecular recognition. A molecular filter such as $\alpha_2$-macroglobulin is added which discriminates between probe reagent so bound and probe reagent which is not so bound. This discrimination occurs either due to the large size of the probe reagent-analyte complex, or due to the effective attachment of probe reagent to immobilized analyte (e.g., analyte bound by a capture reagent comprising an analyte binding molecule coupled to a support). Formation of an essentially irreversible complex between the macroglobulin and probe reagent causes at least partial inactivation of the proteolytic activity of the latter. Thereafter the proteolytic activity of probe reagent bound to analyte is detected, either directly, or optionally after any residual proteolytic activity of probe reagent bound by the macroglobulin is substantially eliminated prior to signal amplification and detection.

Two generic means are disclosed for the effective elimination of such residual activity. One method employs physical separation of probe reagent specifically bound to analyte from probe reagent bound by the molecular filter. A second method employs selective destruction of the proteolytic activity of probe reagent bound by the molecular filter.

In the latter method the proteolytic activity of probe reagent not bound by the molecular filter is first protected by complexing with a reversible proteinase inhibitor. Conversely probe reagent bound by the molecular filter is inherently not appreciably protected. Next substantially all unprotected proteolytic activity is eliminated by treatment with an irreversible proteinase inhibitor (active site titrant). Finally a scavenger proteinase(s) is used to destroy residual active site titrant and active molecular filter, and destroy or competitively displace the reversible inhibitor.

By either of these means the discrimination process of molecular filtering is intensified, permitting advantageous signal amplification and rapid detection of very small amounts of analyte.

A primary object and advantage of my invention is to reduce or substantially eliminate analytical background interference prior to signal detection. This facilitates subsequent rapid exponential amplification of the signal, therefore, potentially, the reliable detection of the presence of one to a few molecules of substance (analyte) within a short period of time. As a result, the invention may be used to quantitatively measure, within a similarly short period, the amount of an analyte, even when present in minute quantities. It is also an object and advantage of the invention to permit such analyses without the need for sophisticated equipment or repetitive manipulations.

The invention, advantageously, is able to function in general within the context of either a homogeneous or heterogeneous assay format, conducted according to either a competitve or non-competitive procedure. It will be apparent to those familiar with the art that the use of the invention, in a preferred embodiment, in a non-competitive, homogeneous assay format, combines the advantages of sensitivity and convenience which have heretofore eluded practical realization.

DETAILED DESCRIPTION OF THE PREFERRED EMBODIMENTS

The present invention relates to affinity binding assays, such as immunoassays and hybridization assays. Such an assay requires an analyte binding molecule, which binds to the analyte to form an affinity complex, and a signal generating system whose signal is somehow dependent on whether or not an affinity complex is formed. In the present invention, the signal generating system includes a proteinase label and a substrate for the proteinase. The proteinase acts upon the substrate so as to generate a detectable signal. In the present invention, a macroglobulin is used to distinguish between free proteinase and proteinase associated with an affinity complex.

Four major classes of proteinases are recognized: the thiol proteinases, such as ficin, papain and bromelain; the carboxyl proteinases, such as pepsin; the metalloproteinases, such as collagenase, aminopeptidase and carboxypeptidase; and the serine proteinases, such as trypsin, chymotrypsin, subtilisin, and pancreatic and neutrophil elastases.

The macroglobulins have been termed "enzyme inhibitors," and it is certainly true that they inhibit the proteolytic action of certain enzymes on certain substrates. However, their mode of action is radically different from that of other proteins which act as proteinase inhibitors. As has been explained in a review article, Laskowski and Kato (1980), this latter group, which includes bovine pancreatic trypsin inhibitor, have class-specific reactive sites, i.e., a given inhibitor will react with only one of the four (carboxyl, metallo, thiol or serine) classes of proteinases. Moreover, in the enzyme-inhibitor complex, all enzymatic activities toward all substrates are totally abolished. Finally, the complex is at least slowly reversible. In contrast, the macroglobulins, such as alpha$_2$-macroglobulin (A2M), affect proteinases of all four mechanistic classes, indeed, it is relatively rare to find endoproteinases which do not form complexes with macroglobulins. In the complex, the active site remains open; the proteolytic activity toward small substrates is almost unimpeded; only the access of larger substrates is hindered. The complex, moreover, is irreversible. Laskowski and Kato conclude their brief review of the macroglobulins by stating, "their interaction with proteinases is so different from that of other protein proteinase inhibitors that at least to chemists their designation as inhibitors seems undesirable."

It is, however, one of these unique characteristics of the macroglobulins that render them useful as signal modulators in a binding assay. In physics, a "filter" is a device which selectively removes or blocks undesired wavelengths of electromagnetic radiation. Molecular filters are a class of proteins which selectively act on at least one proteinase such that its activity with high molecular-weight substrates is substantially reduced, while its activity with low molecular-weight substrates is largely retained. The family of serum proteins called α-macroglobulins is the only known example of molecular filters in nature. The best studied member of this family is $\alpha_2$-macroglobulin (Starkey and Barrett, 1977; Barrett, 1981; Travis and Salvesen, 1983).

When the probe reagent (e.g., a proteinase-labeled analyte binding molecule such as an Fab fragment) is small enough so that the proteolytic activity of the proteinase component is reduced or eliminated by the proteinase-macroglobulin interaction, but the affinity complex (e.g., a complex of analyte and probe reagent) is large enough so that the macroglobulin cannot significantly reduce the proteolytic activity of the proteinase component, the macroglobulin acts as a molecular filter serving to modulate the proteinase-generated signal so that the level of proteolytic activity is an indicator as to the presence or amount of analyte in the sample.

The operation of molecular filtering is explicitly a signal discrimination process whereby non-specific background succumbs to a mechanism which leaves the signal (i.e. specifically analyte-bound proteinase enzyme label) substantially unaffected. Such a process in the present invention advantageously goes to essential completion by virtue of the irreversibility of the reaction between the molecular filter and proteinase. Thus, "the complex with a typical inhibitor dissociates, albeit slowly, while the $\alpha_2$M [$\alpha_2$-macroglobulin] complex is 'irreversible' and does not. The result in an in vitro experiment is that all of the proteinase is ultimately transferred to an α₂M complex, unless there is so much enzyme that α₂M is saturated." (Laskowski and Kato, 1980).

This activity of α₂-macroglobulin is generally believed to result from its physical entrapment of the proteinase molecule (Starkey and Barrett, 1977; Barrett, 1981; Travis and Salvesen, 1983). A wide range of endopeptidases, including serine, cysteine, aspartic and metalloproteinases thereby lose all activity toward many of their natural protein substrates. It is believed that proteinases proteolytically attack a portion of the A2M molecule called the "bait" region. The cleavage of this "bait" region results in a conformational change in the A2M, as a result of which the enzyme is entrapped so that it cannot escape. Molecules of less than 10 KDa freely diffuse through the trap and may bind to the active site, but larger molecules cannot interact with the active site of the trapped enzyme.

When the proteinase is conjugated to another molecule, so that the conjugate is larger than 90 KDa, it is usually no longer susceptible to A2M inactivation. It is believed that the conjugated proteinase still cleaves the "bait" regions, however, the cleaved A2M is not able to entrap the conjugated proteinase.

This operation of molecular signal filtering constitutes the critical step of reduction of background proteolytic activity (i.e., extraneous proteinases and probe reagent not specifically bound to analyte), with minimal degradation of the enzymatic signal (i.e. probe reagent specifically bound to analyte). However, the inactivation of proteinase trapped by the molecular filter is not absolute. Therefore additional components are described below which may be advantageously employed to substantially eliminate all residual proteolytic activity of probe reagent bound by the molecular filter, and residual active molecular filter itself. These measures are generally unnecessary if the molecular filter is physically removed from the analytical environment subsequent to the molecular filtering process.

ASSAY FORMATS

The invention is functional in both substantially aqueous sample solution or suspension (homogeneous assay), and in methods where analyte is present on the surface of a solid or immiscible-liquid phase (heterogeneous assay). Although the invention is functional in general in the presence of solids and solid surfaces, it is advantageous, especially for embodiments employing signal amplification, to minimize micro-porous solids in the analytical environment. This is desirable to prevent access of unbound probe reagent to spaces from which the much larger molecular filter is excluded.

The invention can detect a single analyte, or alternatively any combination of analytes by employing multiple probe reagents, and multiple capture reagents if used.

In the operation of the present invention it is advantageous that exposure of surfaces in the analytical environment to the probe reagent solution be limited to the shortest extent of time which allows substantial binding of same to the analyte. Similarly exposure of the surface to a proteinase solution, if employed to activate a probe reagent which initially has the properties of a zymogen, should be limited to the minimum time necessary to effect activation. Such limitation of exposure time by probe reagent or activating proteinase, prior to their inactivation by the molecular filter, is advantageous to minimize their irreversible, non-specific binding to surfaces in the analytical environment. This type of binding is known to be directly proportional to the duration of exposure of substances to surfaces in general (Andrade and Hlady, 1986). Such bound proteolytic activity is advantageously avoided since it is not substantially susceptible to inactivation by the molecular filter (for the case where α₂-macroglobulin is the molecular filter see Burdon, 1980; Barrett, 1981; Gettins et al., 1988).

While the invention functions in both competitive and non-competitive assay formats the description which follows emphasizes its structure and operation relative to non-competitive protocols due to their greater potential sensitivity. Thus all of the Preferred Embodiments detailed below are non-competitive assays. Only brief descriptions are given of the structure and operation of the invention in competitive assays, since this application will be evident to those skilled in the art as a simple modification of the non-competitive protocols. This approach is intended to minimize unnecessary duplication in the description of the invention, and should not be construed as implying any limitation on its applicability.

All assays require incubation of the sample with a probe reagent. If the probe reagent is not already enzymatically active (i.e. it is a zymogen, proenzyme, apoenzyme or other proteinase precursor), it is next converted to an enzymatically active form by appropriate means as known in the art. For example if it is a zymogen, this is typically activated by exposure to a proteinase. Note that it is essential that the proteinase used to activate the probe reagent, if such is required, either be susceptible to inactivation by the molecular filter, or not interfere with subsequent signal processing or detection steps. As another example, if the probe reagent is an apoenzyme it is activated by allowing it to bind the essential cofactor(s). Other types of activation process can in general be employed, as revealed for example in U.S. Pat. No. 4,745,054 (Rabin et al., 1988).

Thereafter a solution of α₂-macroglobulin or similar molecular filter is added, in stoichiometric excess relative to probe reagent and any extraneous proteinases which may be present. Since α₂-macroglobulin is inactive against proteinases having an effective molecular weight greater than about 90,000 daltons, probe reagent bound to analyte such that the total molecular weight of the complex so formed is greater than this limit is substantially unaffected by the molecular filter. Conversely probe reagent not bound to analyte has a molecular weight less than this limit, and is trapped and selectively inactivated through its interaction with the molecular filter. Such entrapment of probe reagent by α₂-macroglobulin greatly reduces or eliminates its proteolytic activity against most large substrates having an equivalent diameter greater than about 2.5 to 3.0 nm (Barrett and Starkey, 1973). Thus after probe reagent entrapment the degree of effective inactivation depends on the nature of the substrate chosen for proteolytic signal processing and detection.

Non-Competitive Homogeneous Assay. In a non-competitive homogeneous assay format, the sample, possibly containing the analyte, is treated with a solution of a molecule (i.e., a probe reagent) which binds specifically to the analyte through a process of molecular recognition. In the present invention the probe reagent, in addition to its analyte recognition ability, possesses proteolytic activity. In other words the probe reagent consists essentially of an appropriate proteinase (or a precursor thereof) coupled to a molecule capable of molecular recognition of the analyte. The binding of the probe reagent to the analyte results in the formation of an affinity complex which, like the "free" probe reagent, has proteolytic activity.

A macroglobulin is then added to the assay mixture which selectvely reduces the proteolytic activity of the "free" probe reagent relative to the affinity complex. The proteolytic substrate is then added to the mixture, and the proteinase acts on the substrate to generate, directly or indirectly, a detectable signal.

It will be evident that successful operation of the molecular filter in a non-competitive homogeneous assay requires that the molecular weight or size of the complex formed between probe reagent and analyte be sufficient to be substantially unaffected by the molecular filter. Conversely unbound probe reagent must be substantially susceptible to inactivation by the molecular filter. Thus there exists a lower molecular weight or size limit for analyte in order that the invention function satisfactorily in a non-competitive homogeneous assay format. In general analytes of molecular weight less than about 20,000 daltons may be more effectively analyzed by employing the invention in a heterogeneous assay format, or in a competitive homogeneous protocol as described below. For the same reason the molecular weight of the probe reagent should be at least about 75,000 daltons for non-competitive homogeneous assay of substances having a molecular weight of about 20,000 daltons. In other words the total molecular weight of the probe reagent-analyte complex should be at least about 95,000 daltons, and preferably 100,000 daltons, for satisfactory operation of the invention in such non-competitive homogeneous assays.

The lower molecular weight limit of about 20,000 daltons for operation of the invention in a non-competitive homogeneous assay protocol complements the (competitive) homogeneous assay systems in current commercial use. Thus, "most homogeneous immunoassays can measure only analytes that are small molecules...Systems such as EMIT by Syva Corporation and TDx by Abbott Laboratories can measure only small molecules such as drugs and thyroxine." (Chan, 1987) The invention therefore achieves the previously elusive goal of analysis by a homogeneous assay method for medically important microbial pathogens, all of which are of very large size on a molecular scale.

Competitive Homogeneous Assay. For substances which are too small to be analyzed by a non-competitive homogeneous protocol, a competitive assay can be employed.

In a competitive homogeneous assay the components and steps of the invention are the same as above with the exception that the probe reagent comprises an analyte analogue conjugated to an appropriate proteinase. Thus the probe reagent can compete with analyte for binding to a third substance (effectively a soluble analyte binding molecule) through a process of molecular recognition.

In one such scheme the analyte is coupled to a suitable proteinase such as trypsin. This labelled-analyte conjugate (i.e. probe reagent) competes with actual analyte for specific binding sites on a limiting amount of an appropriate antibody, nucleic acid, etc. (i.e. a soluble capture reagent). Thereafter any unbound probe reagent is entrapped and selectively inactivated with a solution of molecular filter. The proteolytic signal bound to the capture reagent is then processed or detected as usual. In this scheme, as is typical of competitive assays, the final signal level is inversely proportional to the amount of analyte present in the sample.

Non-Competitive Heterogeneous Assay. In a heterogeneous assay the operation of the invention takes place in the presence of at least one solid surface on which one or more members of the relevant affinity complex are immobilized. Many of the numerous heterogeneous immunoassay protocols proposed were reviewed by Ngo (1985). A useful review of various types of heterogeneous nucleic acid assays is that of Nicholls and Malcolm (1989).

In most heterogeneous analytical protocols which employ a process of molecular recognition of the analyte in at least one step, a capture reagent is provided in which a suitable binding molecule is essentially irreversibly bound to a solid surface by any of several methods known in the art. Such binding may be achieved by forces commonly designated as physical or chemical, or some combination thereof. Such capture reagents are discussed in detail below.

Next the liquid sample possibly containing the analyte is placed in contact with the surface for a period of time sufficient to allow binding of analyte to the capture reagent by means of a molecular recognition process. Preferably, after the affinity complex of capture reagent and analyte is formed, non-specifically bound and free interferents are advantageously removed to the extent feasible by simple washing. Next the surface is exposed to a solution of probe reagent, which binds specifically to the analyte through a molecular recognition process, and non-specifically to surfaces in the analytical environment. After probe reagent application the surface is again advantageously washed briefly.

In the next step the macroglobulin is added, whereby any probe reagent not specifically bound to the immobilized analyte is entrapped and at least partially inactivated.

Although $\alpha_2$-macroglobulin reacts quickly with proteinases in solution (e.g. reaction half-time versus trypsin of about 0.05 seconds), it has very little activity toward immobilized trypsin or chymotrypsin (Barrett, 1981). Thus chymotrypsin bound to agarose reacted to partially inactivate $\alpha_2$-macroglobulin, but fewer than 6 per cent of the reactions successfully removed the bound proteinase (Gettins et al., 1988). A similar result for trypsin has also been reported (Burdon, 1980). Thus even if at most a few specifically-bound signal probes are present it is a virtual certainty that at least one will survive treatment with $\alpha_2$-macroglobulin. Absolute quantitation can be readily calibrated by using known standards to compensate for the slight effect of $\alpha_2$-macroglobulin on bound proteinase.

Following completion of the molecular filtering process the proteolytic signal of probe reagent bound to analyte can be detected or further processed, including optional elimination of the proteolytic activity of probe reagent bound by adsorbed molecular filter, and inactivation of residual active molecular filter, as previously described.

Competitive Heterogeneous Assay Format. In a competitive heterogeneous assay format, the probe reagent is as described above for competitive homogeneous assay. However, the steps are otherwise the same as described above for a non-competitive heterogeneous assay format.

Signal Amplification. The invention provides assays for substances subject to molecular recognition (e.g.

antigens, antibodies and nucleic acids) whose combined sensitivity and rapidity are greatly increased by enzymatic reduction of background interference. These advantageous features are most effectively realized in embodiments which employ exponential signal amplification prior to measurement.

Several methods are potentially capable of amplifying a proteolytic activity signal, or transforming it to another form of enzymatic activity or other analytical marker. Likewise numerous methods are available in the art for measurement of the activity of the various proteinases which could be incorporated into probe reagents.

A preferred means of signal amplification employs a zymogen capable of what is commonly termed autoactivation. For example, the zymogen, trypsinogen, is converted to an active proteinase by the proteolytic activity of the bound probe reagent(s); and the proteinase so formed activates further zymogen. The zymogen solution in preferred embodiments contains substances such as surfactants and metal ions which increase the activation rate as known in the art. This autocatalytic process produces an essentially exponential increase in proteolytic activity with time. Thereafter the proteolytic activity present is measured by any of several means, of which a chromogenic substrate and spectrophotometric detection is an especially convenient method.

Reduction of Background. After the macroglobulin has been allowed to interact with free probe reagent, there may still be residual active macroglobulin, and the entrapped probe reagent may possess some residual proteolytic activity. After the process of molecular filtering has been completed the analytical environment may be treated with a reversible inhibitor, active site titrant, and scavenger proteinase(s) as described below to substantially eliminate residual active molecular filter and any proteolytic activity bound by the molecular filter. Alternatively, in embodiments where the molecular filter is immobilized on a solid, this may be physically separated from the assay mixture prior to further signal processing or detection steps.

ANALYTICAL SAMPLES

The sample may be any material which potentially contains an analyte of interest for which an affinity binding molecule is available. Samples include animal (incl. human) and plant tissues, organs and fluids (including, in the case of animals, blood, urine, milk, and cerebrospinal fluid), food and beverages, solid and liquid wastes, and soil, ground water, and seawater.

Preferably, the material is first prepared in buffer having a pH generally between about 6.0 and 8.5. For substantially solid or hydrophobic samples, the sample is dispersed in similar concentrated buffer, possibly with added surfactant(s). If colloidal or larger solids are present the sample is aseptically filtered, for example through fine, acid-washed filter paper.

The sample may contain one or several analytes. Typical analytes include, but are not limited to viral, microbial, plant and animal antigens, receptors and nucleic acids. In general, the analyte may be any material for which a specific binding molecule is available which when conjugated to a proteinase label, forms a proteolytically active conjugate susceptible to inactivation by a macroglobulin, and which, when bound to the analyte, forms an affinity complex which is less susceptible to such inactivation. Lists of analytes for which binding assays have been contemplated may be found in many U.S. patents, e.g., Zuk, U.S. Pat. No. 4,281,061.

If there are proteinases in the sample which are not susceptible to the molecular filter, a control performed as described above but omitting the probe reagent will give substantially the same result as in the actual assay. Such interfering proteinases can then be inactivated prior to re-analysis. Such inactivation can be achieved by any of several means known in the art, provided that any residues in the sample from the inactivation process do not substantially interfere subsequently with the enzymatic activity of the probe reagent. For example, where the molecular filter used is $\alpha_2$-macroglobulin, and the sample contains enteropeptidase or other serine proteinases not susceptible to inactivation by $\alpha_2$-macroglobulin, these contaminating proteinases can generally be inactivated by treatment with diisopropyl fluorophosphate (cf. Barrett and Salvesen, 1986). Alternatively, enteropeptidase activity contaminating the sample can be conveniently eliminated by heating at 60° C. for 2 minutes (Anderson et al., 1977).

Conversely if there is $\alpha_2$-macroglobulin initially present in the sample (e.g. blood), this can be inactivated by adding a slight excess of a scavenger proteinase (see below) prior to analysis.

Special cases may occur if the analyte is a proteinase, macroglobulin or proteinaceous proteinase inhibitor. Proteinases may be assayed using an active site titrant or immunological probe reagent provided that the proteinase does not interfere, or can be prevented from interfering, with signal processing or detection. Macroglobulins may be assayed without complication, using a lectin or Fab'-type probe reagent, if they are first rendered inactive by use of a scavenger proteinase (see below). Proteinaceous proteinase inhibitors may be assayed, unless present in very high concentration, using an immunological probe reagent: at reasonably low concentration the analyte will only delay the molecular filtering and signal generation steps.

SIGNAL PRODUCING SYSTEM

In its most elementary form, the signal producing system comprises a proteinase label (usually conjugated to an analyte binding molecule to form a probe reagent, infra), a substrate for the proteinase, and a macroglobulin modulator of the proteolytic action of that proteinase on that substrate which is sensitive to whether the probe reagent has bound the analyte to form an affinity complex.

An especially suitable proteinase for fabrication of probe reagents is trypsin, which reacts rapidly with $\alpha_2$-macroglobulin (Barrett, 1981), has a low molecular weight of about 24,000 daltons, and maximal activity in the pH range of about 7 to 8 (Walsh, 1970). A further advantage of trypsin as probe reagent proteinase is its ability to activate the amplification zymogen, trypsinogen, in embodiments in which this is employed. Porcine trypsin is especially favoured due to its relative thermal and autolytic stability (Lazdunski and Delaage, 1965). Certain derivatives of trypsin also might be useful in this regard. For example Walsh (1970) reports that trypsin is stabilized against autolysis by acetylation; and Keil (1971) states that such derivatives possess the same activity as native trypsin toward synthetic substrates. Several other derivitization methods are known in the art which are potentially applicable to stabilization of proteinases against autolysis (cf. Means and Feeney, 1971, p. 45).

The macroglobulin may be free in solution, or coupled to a soluble or insoluble substance.

Following molecular filtering the proteolytic signal of probe reagent bound to analyte can be detected directly, or advantageously processed before detection. A selection is given below from the wide range of signal processing methods which can be applied in conjunction with the invention.

In one scheme probe reagent trypsin converts inactive chymotrypsinogen to active chymotrypsin which is detected colorimetrically or by other means known in the art (Worthington, 1988). Several other zymogens which can be activated by trypsin or other proteinases susceptible to a molecular filter can be similarly employed. A preferred scheme uses trypsinogen as the signal processing (amplification) zymogen in conjunction with probe reagent which is a trypsin conjugate, as described below.

In another scheme cathepsin B is the proteinase used to fabricate probe reagent. After molecular filtering aldolase is added, and inactivated by the probe reagent proteinase during an incubation period (Barrett and McDonald, 1980). Thereafter residual aldolase, inversely proportional to the amount of active cathepsin probe reagent present, is assayed by ultra-violet spectroscopy using fructose-1,6-diphosphate and hydrazine as substrate and chromogen respectively (Worthington, 1988). A conceptually identical signal processing scheme employs any of a number of molecular filter-susceptible probe reagent proteinases to inactivate luciferase, whose residual activity is then measured (Njus et al., 1974; see Preferred Embodiment No. 2).

Another scheme uses the proteolytic activity of probe reagent to activate a second enzyme by means of a cofactor or coenzyme. Thus a coenzyme or its precursor such as thiamine, riboflavin or pyridoxal can be derivitized via an amide or ester bond such that coenzyme activity is blocked. Cleavage by probe reagent proteinase of this bond restores coenzyme activity, leading to activation of an apoenzyme which produces a detectable result on incubation with a suitable substrate. Several examples of appropriate enzyme-coenzyme systems are given in U.S. Pat. No. 4,745,054 (Rabin et al., 1988).

Uses of proenzymes, apoenzymes and zymogens as labels are described in Taub, U.S. Pat. No. 4,820,630, Ledden, U.S. Pat. No. 4,810,635, Ashida, U.S. Pat. No. 4,970,152, Siddiqui, U.S. Pat. No. 4,960,693, Libeskind, U.S. Pat. No. 4,699,876.

Other schemes can use the proteolytic activity of the probe reagent to achieve amplification by cleavage of a "substrate leash" (cf. Ehrat et al., 1986), or by rupture of a polypeptide membrane encapsulating enzymes or other analytical markers (e.g. fluorescein, radionuclide; cf. Litchfield et al., 1984). In the former method, for example, the two inactive fragments of ribonuclease can be separately immobilized via a polypeptide "leash" or linker arm. Proteolytic cleavage of this leash allows the inactive fragments to combine into active ribonuclease which is then detected. In the latter method an enzyme or other analytical marker is simply entrapped inside a protein or polypeptide membrane, whose rupture directly or indirectly by the proteolytic activity of probe reagent leads to signal amplification and a detectable result.

In either of the latter schemes it will be obvious to those skilled in the art that the polypeptide leash or membrane can be tailored to match the specificity of the proteinase incorporated in the probe reagent. Alternatively, a preliminary enzyme cascade can be used to achieve further amplification or transformation of the signal to a different proteolytic specificity if desired. For example, probe reagent trypsin can transform inactive proelastase to elastase which cleaves a leash or membrane composed of elastin or similar polypeptide (Barrett and McDonald, 1980).

From these examples it will be evident that a wide range of signal processing schemes are applicable in conjunction with the invention. The examples cited are representative possibilities rather than an exhaustive catalogue, and in no sense to be construed as implying any limitation on the invention with respect to signal processing following molecular filtering.

In a preferred embodiment the signal associated with analyte is advantageously increased by use of an amplification zymogen system, i.e. by the proteolytic action of the probe reagent bound to analyte, if such is present, molecules of amplification zymogen (i.e. proteinase precursor) are converted to active proteinase. Moreover the proteinase thus formed converts further amounts of the zymogen to an active form resulting in an essentially exponential increase with time in the amount of active proteinase present (Pechère and Neurath, 1957). A preferred embodiment employs trypsin as the proteinase moiety of the probe reagent, and trypsinogen as the amplification zymogen, wherein the rate of activation is greatly increased by addition of various surface active agents and metal ions (Sarkany and Moreland, 1985; Moreland and Sarkany, 1985; Moreland et al., 1985; Moreland and Sanyal, 1985). By calibration with standards to estimate the rate constant (Pechère and Neurath, 1957), or the time required for a certain degree of zymogen activation (Mayer et al., 1974), quantitative determination of the active proteinase initially present can be made.

ANALYTE BINDING MOLECULE

As previously stated, this invention relates to improved affinity binding assays, in which a binding molecule having an affinity for the analyte binds to it to form an affinity complex. Typically, non-limiting examples of possible affinity complexes are antibody (or antibody fragment): antigen, nucleic acid: nucleic acid, enzyme: substrate, and biologically active molecule: natural receptor.

The binding of the analyte binding molecule to the analyte should ideally be essentially irreversible, i.e., the average duration of the complex so formed is preferably of at least similar magnitude to the time required for "molecular filtering". Such binding is generally believed to occur through the concerted effect of a large number of hydrogen bonds and so-called hydrophobic interactions. Although I do not wish to be bound by this theory, the effective irreversibility of this binding is thought to be due to a synergistic interaction amongst a typically large number of weak bonds (Stenberg and Nygren, 1988).

In one preferred embodiment, the analyte is an antigen (which may itself be an antibody) and the binding molecule is a derivative of an antibody. For reasons explained elsewhere, a whole antibody is not suitable. Since the required immuno-reactive fragments for the vast majority of analytes of practical interest are not commercially available they can be produced by proteolytic cleavage of the appropriate immunoglobulin G (IgG). If the latter is unavailable, high-affinity polyclonal or monoclonal IgG for the desired analyte can be produced and purified by methods known in the art. Given a supply of IgG appropriate to the analyte, the desirable intermediate F(ab')2 fragment is readily prepared by proteolytic digestion of IgG, generally using pepsin (Parham et al., 1982; Lamoyi, 1986; Rousseaux et al., 1986; Parham, 1986). A typical pepsin digestion procedure is described in the Reference Example.

ANALYTE ANALOGUE

The term "analyte analogue" refers to a substance which is able to compete with the actual analyte for binding to an analyte binding molecule used as a reagent in the assay. The epitome of an analyte analogue is, of course, a duplicate of the analyte itself, however, a related substance which retains the essential binding characteristics of analyte but which has been modified, e.g., for ease of coupling to a proteinase label, may be employed.

PROBE REAGENT

The probe reagent is a conjugate of a proteinase label (or suitable precursor) to a "probe" moiety, which is either an analyte binding molecule (for a noncompetitive assay) or an analyte analogue (for a competitive assay), and which binds to a "target" to form an affinity complex. For the sake of simplicity, the following discussion will refer to the label as being conjugated to an analyte binding molecule. However, it should be understood that the comments apply, *mutatis mutandis*, to proteinase-(analyte analogue) conjugates as well. It should further be noted that the use of the term "probe" is not intended to suggest a limitation of the concept to nucleic acid hybridization probes.

Whatever the coupling means employed, the following considerations apply: (1) the coupling should not substantially reduce the ability of the proteinase to recognize and cleave its substrate, or the ability of the analyte binding molecule to bind to analyte, and (2) the conjugate must be susceptible to modulation of proteolytic activity by the macroglobulin employed. Where $\alpha_2$-macroglobulin is the molecular filter, the proteinase must be reactive with $\alpha_2$-macroglobulin.

Many proteinases are known to be trapped by human $\alpha$2-macroglobulin:
Serine Proteinases
  Chymotrypsin (26 kD)
  Trypsin (23.8 kD)
  Thrombin (37.7 kD)
  Plasmin (catalytic subunit is 25 kD)
  Plasma Kallikrein (catalytic subunit is 36 kD)
  Acrosin (38 kD)
  Pancreatic Elastase (25.9 kD)
  Leukocyte Elastase (30 kD)
  Cathepsin G (30kD)
  Arvin (*Agkistrodon rhodostoma* coagulant)
  Batroxobin (*Bothrops atrox* venom coagulant)
  Chymotrypsin-like proteinase (*Schistosoma mansonii*)
  Brinase (*Aspergillus oryzae* Proteinase I)
  Serratia spp. E15 proteinase
  *Staphylococcus aureus* "acid" proteinase
  *Stachylococcus aureus* V8 proteinase (12 kD)
  Subtilisins A and B (28 kD)
Thiol (Cysteine) Proteinases
  Cathepsin B (25 kD)
  Cathepsin H (28 kD)
  Cathepsin L (24 kD)
  Calcium-dependent proteinase
  Papain (22 kD)
  Ficin (23.8 kD)
  Bromelain (32 kD)
  Clostripain
Carboxyl (Aspartic) Proteinases
  Chymosin (35.6 (kD)
  Cathepsin D (42 kD)
  Periplaneta acid proteinase
Metalloproteinases
  Vertebrate Collagenases (35 kD/65 kD)
  Leukocyte Collagenases (6I kD)
  *Crotalus atrox* venom proteinase
  *Crotalus adamanteus* venom proteinase
  *Trichophyton mentagraphytes* keratinase (34.3 kD)
  *Pseudomonas aeruginosa* elastase
  Thermolysin (37.5 kD)
  *Bacillus subtilis* metalloproteinase
Unknown Mechanism Proteinases
  *Proteus vulgaris* neutral proteinase
  *Fusiformis nodosus* neutral proteinase The molecular weights for some of the susceptible proteinases are given parenthetically in the above table. The largest proteinases reported to be bound are plasma kallikrein and plasmin, both about 90,000 D.

The absolute rate of trapping varies depending on the proteinases. The half-time for binding of trypsin at moderate concentrations of enzyme and A2M were reported to be 0.05 secs for trypsin, and 30 min for thrombin and plasma kallikrein. Havell, et al. (1983) reports that for four common proteinases the order of rate of reaction is papain > trypsin > chymotrypsin > plasmin. Fast-reacting proteinases, such as papain, trypsin, chymotrypsin and elastase, are preferred. The rate of reaction may be decreased by competing substrates or inhibitors, but since A2M trapping is irreversible, even a very tight but reversible complex with an enzyme inhibitor will be dissociated eventually.

The preferred proteinase will vary depending on the nature of the "probe" and "target". If the probe is of relatively high molecular weight, as in the case of an Fab fragment, the preferred proteinase is of low molecular weight so that the probe reagent is readily entrapped. If the probe is of relatively low molecular weight, as may be true of a nucleic acid, use of a higher molecular weight proteinase becomes feasible. If the target is of high molecular weight, then a considerable number of possible probe reagents may exist which satisfy the criteria of being small enough to be affected by A2M when free, but too large to be entrapped after they bind their target. When the target is small, the probe reagent must be appropriately closer in size to the cutoff molecular weight.

The worker is not limited to proteinases which exist in nature. If a natural proteinase is too large to serve in a probe reagent, it may be replaced by a proteolytically active fragment. Mutations may be made to increase the rate of trapping, e.g., by modifying the active site to more closely resemble that of a more reactive proteinase. If a proteinase is too small to escape trapping in the affinity complex, it may be bulked up by conjugating it to a noninterfering carrier.

A further consideration is the choice of A2M. Mammals, birds, reptiles and amphibia all have an A2M-like protein (as judged by the capacity to trap papain) of similar size to human A2M. The corresponding protein in fish is smaller, but nonetheless operates the trap mechanism. Any naturally occurring or mutant macroglobulin capable of acting as a molecular filter may be used.

Preferably, the total molecular weight of the probe reagent should not exceed about 90,000 daltons, as it is presently believed that only proteinases of about 90,000 daltons or less are susceptible to modulation by human $\alpha_2$-macroglobulin (Barrett, 1981). However, if susceptible proteinases of higher molecular weight are identified, then this constraint on the size of the probe reagent may be appropriately relaxed.

Conjugation Methods. In general, the probe reagent is formed by covalently coupling the proteinase label to the analyte binding molecule. However, noncovalent coupling means may be employed if, under the assay conditions, the label and the analyte binding molecule will not be dissociated.

In general, covalent coupling will be accomplished by a chemical reaction between the proteinase label and the analyte binding molecule.

While it is possible that both the label and the analyte binding molecule will already possess reactive sites, so that the two may be reacted directly, more often either the proteinase, or the analyte binding molecule, or both, will need to be activated by reaction with a reagent that makes them more reactive. In some cases, both the proteinase label and the analyte binding molecule will be reacted with a bifunctional reactive linker, either sequentially or simultaneously. When the reaction is simultaneous, it is preferable to use a heterobifunctional linker one end of which reacts only with proteinase molecules and the other only with the analyte binding molecules, so that only the desired conjugate is formed.

Numerous methods are available for coupling enzymes to proteins, especially immunoreactive substances. (cf. Tijssen, 1985). Preferred procedures for coupling a proteinase to a Fab' fragment employ an N-hydroxysuccinimide ester of a maleimide derivative as the coupling reagent in a two-step process. Two especially effective reagents are 4-(N-maleimidomethyl)-cyclohexane1-carboxylic acid N-hydroxysuccinimide ester (CHM-NHS) (Yoshitake et al., 1979, 1982; Imagawa et al., 1982; Ishikawa et al., 1983), and N-(gamma-maleimidobutyryloxy)succinimide (GMBS) (Fujiwara et al., 1981; Kitagawa et al., 1983; Aoyagi et al., 199). In these methods the amino group of the proteinase is first reacted with the coupling reagent, and the activated proteinase purified. The latter is then coupled by reaction with a thiol group of the Fab' fragment. It is advantageous to minimize autolysis of the proteinase in the first step by employing a proteinase inhibitor such as 4-aminobenzamidine, which contains no reactive amino group. This also to some extent protects the potentially reactive amino group(s) of the active site. During the coupling step per se the same or another proteinase inhibitor can be used to minimize both autolysis and proteolysis of the Fab' moiety.

When the analyte binding molecule is a peptide or protein, since the proteinase is a polypeptide, it is possible that a suitable conjugate could be produced through a process of genetic engineering (see for example Kobatake et al., 1990). That is, a fusion protein is expressed which comprises both an analyte binding domain and a proteinase domain, optionally joined by a linker of one or more amino acids. If this approach is undertaken, the linker is preferably rich in glycine (which imparts flexibility) and/or proline (which provides the maximum separation).

Several methods are available for coupling enzymes to oligonucleotides, including coupling with disuccinimidyl suberate via a modified thymine base containing a "linker arm" (Ruth et al., 1985; Jablonski et al., 1986; Ruth and Jablonski, 1987); coupling with glutaraldehyde and p-benzoquinone via polyethyleneimine (Renz and Kurz, 1984); and coupling via a thiol group introduced into an oligonucleotide by means of a cystamine compound (Cheng et al., 1983), or present in a commercially available nucleotide (described below under Preferred Embodiment No. 4). Further methods which could be applied to enzyme-oligonucleotide coupling by one knowledgeable in the art are also available (Cosstick et al., 1984; Connolly, 1985; Sproat et al., 1987, 1988). Since oligonucleotides are not susceptible in general to proteolysis, no particular problem is encountered in coupling them to a proteinase if simple precautions are taken to minimize autolysis of the latter. Proteinase-oligonucleotide conjugates possessing only essentially active enzyme are readily obtained by affinity chromatography on an immobilized proteinase-inhibitor column as described under "Immuno-reactive Probe reagent".

Preferred Conjugates. In one embodiment suitable for immunoassays, trypsin or other low molecular weight proteinase is coupled to an immuno-reactive Fab' fragment (or other immuno-reactive fragment) by any of several methods known in the art. Such a trypsin conjugate has a total molecular weight of about 75,000 daltons, and is therefore susceptible to inactivation by $\alpha_2$-macroglobulin. On the other hand a conjugate of trypsin with whole immunoglobulin G would have a total molecular weight of approximately 170,000 daltons, and would therefore not be susceptible to inactivation by $\alpha_2$-macroglobulin.

In another embodiment, suitable for nucleic acid hybridization assays, trypsin or other suitable proteinase is coupled to an oligonucleotide (either DNA or RNA) by any of several methods known in the art. Where $\alpha_2$-macroglobulin is the molecular filter, and the proteinase to be employed for coupling is trypsin, it is essential that the oligonucleotide have a molecular weight not greater than about 66,000 daltons, and preferably less than about 56,000 daltons (i.e. about 80 nucleotide units). This requirement is necessary for the proteolytic activity of the trypsin-oligonucleotide probe reagent to be susceptible to inactivation by $\alpha_2$-macroglobulin. DNA or RNA oligonucleotides appropriate for detection of any desired nucleic acid sequence are readily prepared from commercially available materials by chemical and/or biochemical methods well known in the art (see for example Narang, 1987).

It will be evident to those skilled in the art that a functional probe reagent could ultimately be obtained by substituting a proteinase precursor or zymogen for the proteinase label. The probe could then be activated (e.g. by proteinase treatment) either before or after binding to the analyte. Such a probe reagent thus becomes functionally equivalent to those described above, provided that this activation is performed before treatment with the molecular filter, macroglobulin.

Incubation Period. During an incubation period, the background signal, due essentially to probe reagent not specifically bound to analyte, is substantially reduced with minimal degradation of the signal associated with analyte. Proteinases vary in the rate at which they react with $\alpha_2$-macroglobulin, having binding half-times ranging from less than 0.05 seconds to 30 minutes (Barrett, 1981; cf. Howell et al., 1983). With preferred probe reagent proteinases such as trypsin several minutes are allowed to ensure substantial background reduction, although this period can be varied by adjustment of the concentration of molecular filter used.

Special considerations. When the analyte is a small molecule, it may not render the molecular weight of the affinity complex sufficiently greater than that of the probe reagent to achieve the desired modulation of proteinase activity. In this situation, a secondary reagent (e.g., a "capture reagent") which binds the analyte may be used to increase its effective molecular weight. If the binding of this secondary reagent results in the masking of all effective epitopes on the analyte for binding by the probe reagent, the probe reagent may instead be designed to bind an epitope formed by the complexing of the secondary reagent with the analyte. Alternatively, the assay may be conducted in a competitive format as previously discussed.

PROTEOLYTIC SUBSTRATES

The proteinase label generates a signal through its action on a substrate which is cleavable by that proteinase. While the substrate necessarily contains one or more susceptible amide or ester bonds, it may also comprise a peptidyl or nonpeptidyl moiety which does not interfere with the proteolytic effect, i.e. the substrate must provide the appropriate cleavage site(s) in accessible form. Unless A2M-trapped proteinase is removed prior to signal generation, the substrate must be one which is more readily cleaved by untrapped (complexed) proteinase than by A2M-trapped (uncomplexed) proteinase. Generally speaking, substrates in excess of 10,000 Daltons molecular weight are essentially completely excluded from interaction with A2M-trapped proteinase. However, smaller substrates may also be excluded to a useful degree; this may be determined by testing. We have found that $N_\alpha$CBZ-L-lysine thiobenzyl ester, which has a molecular weight of less than 1,000 Daltons, is in fact so excluded.

The product of the proteolytic action may be detectable directly, or it may in turn cooperate with additional enzymes and substrates of the signal producing system to generate a signal.

Zymogenic substrates. In a preferred embodiment, the substrate is a zymogen (inactive enzyme precursor) capable of conversion to active proteinase by the proteolytic activity of the probe reagent(s). Use of a zymogen substrate permits enzymatic amplification of the proteolytic activity of probe reagent bound to analyte. In order to acheive the lowest possible detection limit for analyte by this amplification method, it is necessary that the zymogen solution be essentially devoid of proteinase activity prior to its application.

Suitable zymogens completely devoid of proteinase activity are not known to be commercially available, but are readily prepared by any of several methods known in the art. For example, commercial trypsinogen (zymogen) is typically contaminated with up to several per cent of trypsin (proteinase). Although such contamination can generally be reduced, for example by chromatography on an immobilized trypsin-inhibitor column, its essential elimination is most effectively achieved by use of a soluble, irreversible trypsin inhibitor. Several of the latter are known in the art, including diisopropyl fluorophosphate (DFP; Kay and Kassell, 1971), $N_{6\alpha}$-tosyl-L-lysine chloromethyl ketone (TLCK; Shaw et al., 1965), and $\alpha_2$-macroglobulin (Barrett, 1981).

A preferred reagent for elimination of trypsin activity from commercial trypsinogen is phenylmethylsulfonyl fluoride (PMSF) due to its relatively low toxicity, its low cost and ease of removal. Thus, low-trypsin trypsinogen (Worthington Biochemical Corp., Freehold, N.J.), containing about 0.075% trypsin, is dissolved at a concentration of about 0.20 to 0.36 mM in 0.2M phosphate buffer, pH 7.0, and PMSF (50 mM in isopropanol) is added to a concentration of 3mM. After thorough agitation the mixture is allowed to stand overnight at room temperature. The supernatant is dialyzed at 4° C. against several changes of 50 mM phthalate buffer, pH 3.5. The purified trypsinogen solution can then be stored for long periods at $-20°$ C., preferably in aliquots of volume sufficient for no more than a single day's requirement.

MEASUREMENT OF PROTEOLYTIC ACTIVITY

In the final analytical step the amount of active proteinase present is determined by any of several methods known in the art. Such methods include, but are not limited to, conversion of a proteinase substrate to a product typically measured by colorimetry, spectrophotometry, fluorometry, acidimetry, galvanometry, manometry, scintillation, chromatography or electrophoresis. A convenient, 10 minute spectrophotometric procedure is described by Moreland and Sanyal (1985), including an optional stopping method advantageously employed for quantitative analysis.

CAPTURE REAGENT

In a heterogeneous (i.e. surface-mediated) assay format an additional component is required, a "capture reagent". This capture reagent is an analyte binding molecule which has been associated with a suitable support, i.e., a solid or immiscible liquid surface. Preferably, the capture reagent is formed through the adsorption or covalent attachment of an analyte binding molecule to a solid support. This support may be made of any material conventionally used in the binding assay art, e.g., polyethylene, polystyrene, nitrocellulose, nylon, and glass, and may be fabricated in any convenient form, such as a test tube, dipstick, well or strip. ELISA (enzyme-linked immuno-sorbent assay) and most oligonucleotide probe hybridization assays (e.g. so-called "sandwich-type" assays) are characterized by such an immobilization procedure.

The specificity of the capture reagent is preferably improved by blocking non-specific binding sites (e.g., an empty patch on the solid support) with a non-interfering substance(s), such as skim milk or bovine serum albumin (Pruslin et al., 1991).

It is also generally desirable to remove analyte binding molecule not irreversibly bound to the surface by washing, preferably repeatedly, with an appropriate buffer solution, preferably containing a surface active agent, in order to remove non-bound capture reagent and other potential interferents (Mohammad and Esen, 1989).

REDUCTION OF BACKGROUND SIGNAL

Reduction of Background due to Nonspecific Binding of Proteinase to the Support. In a heterogeneous assay, sensitivity may be reduced as a result of nonspecific binding of the probe reagent (or extraneous proteinases in the sample) to the support used in the formulation of the capture reagent. Although I do not wish to be bound by this theory, the selective activity of $\alpha_2$-macroglobulin toward non-specifically bound proteinases is believed to arise from the effective reversibility of such binding. Thus, during at least the first several minutes of exposure, the residence time of non-specifically bound (adsorbed) protein on a typical analytical surface is in the range of milliseconds to seconds (Lin et al., 1989). Such protein is rapidly interchanged between bound and free forms, the latter susceptible to $\alpha_2$-macroglobulin near the surface. In this context it is advantageous to exploit the Vroman effect whereby a relatively high concentration of a high binding-affinity substance competitively displaces adsorbed protein (Andrade and Hlady, 1986). Examples of such substances are serum proteins, especially fibrinogen and fibronectin (ibid.). Thus, serum proteins may be used to reduce the residence time of non-specifically bound proteinases on a capture reagent and thereby increase their susceptibility to the macroglobulin.

Thus in one preferred embodiment, surfaces in the analytical environment, having a combination of non-specifically bound interferents and possibly signal probes explicitly immobilized via analyte, are exposed to an approximately 10 mg/l solution (about $1.4 \times 10^{-8}$ M) of $\alpha_2$-macroglobulin in 0.1M phosphate buffer, pH 7.0, containing about 1%W/V rehydrated bovine serum, and 0.02%W/V Tween TM 20 (Tween is a registered trademark of ICI Americas, Inc., New York, N.Y.). The reaction is typically allowed to proceed for about 20 minutes at room temperature, although the period may be 5 to 30 minutes or more depending on the concentration of active molecular filter added at room temperature.

Reduction of Background due to Residual Proteolytic Activity of Macroglobulin-Entrapped Proteinases. Although entrapped and generally inaccessible to proteins of molecular weight larger than about 9,000 to 10,000 daltons, the proteinase may retain some activity toward substrates of higher molecular weight.

For example, trypsin bound by $\alpha_2$-macroglobulin loses all activity towards most high molecular-weight and undenatured proteins, but retains significant activity even against some relatively large proteins (Rinderknecht and Geokas, 1973). Thus, "Presumably nonspherical parts of molecules such as zymogens, fibrinogen, and fibrin gain access to the catalytic sites of proteinases complexed to $\alpha_2$-M [$\alpha_2$-macroglobulin], allowing low levels of hydrolysis" (Davies, 1976). This phenomenon presents no problem, for example, in measurement of trypsin or papain probe reagent activity with large substrates such as dye-impregnated collagen (Rinderknect and Geokas, 1973; Howell et al., 1983). However additional measures to increase the effectiveness of molecular filtering are desirable in certain preferred embodiments which employ a zymogen such as trypsinogen to amplify the proteolytic signal.

Various means, in general applicable to both homogeneous and heterogeneous assays, are available to reduce or effectively eliminate this limitation. One means is to use a molecular filter immobilized on a solid surface, and remove the sample solution from contact with same after completion of the molecular filtering process. An example of the operation of this method is described in Preferred Embodiment No. (cf. No. 4). In another variation of this method a soluble molecular filter is physically removed from the analytical environment after its typical reaction with the probe reagent. This can be achieved, for example, by use of an appropriate antibody or lectin specific for the molecular filter, and immobilized on a solid to enable its physical removal (see for example Harpel and Hayes, 1980). Another method for elimination of residual proteolytic activity of probe reagent bound by the molecular filter employs cells such as fibroblasts (Van Leuven et al., 1979, 1981), macrophages (Kaplan and Nielsen, 1979), neutrophils, or monocytes (Wilkinson, 1988). Such cells effectively bind $\alpha_2$-macrolobulin-proteinase complexes, but generally not active macroglobulin.

Another means for substantially eliminating the residual proteolytic activity of probe reagent bound by the molecular filter, as well as residual active molecular filter, employs the differential properties of various types of proteinase inhibitors and proteinases. Specifically an active site-directed reagent (active site titrant) is used to destroy proteolytic activity bound by the molecular filter, while probe reagent not so bound is protected by a suitable reversible proteinase inhibitor. Such selective inactivation can be achieved by use of a reversible inhibitor which is effectively excluded from access to probe reagent bound by the molecular filter. Finally a scavenger proteinase or proteinases can be used to inactivate residual active molecular filter and active site-directed reagent, and destroy or effectively displace the reversible inhibitor.

Thus, an especially effective method for elimination of residual active molecular filter, and any residual proteolytic activity of probe reagent bound by molecular filter, employs three components. In order of use the first component is an essentially reversible inhibitor of the probe reagent's proteolytic activity. It is critical that this inhibitor not interact appreciably with probe reagent bound by the molecular filter. Suitable inhibitors thus have a molecular weight not less than about 9,000 daltons (Laurell and Jeppsson, 1975), and include $\alpha_1$-antitrypsin ($\alpha_1$-antiproteinase; Heidtmann and Travis, 1986), Kunitz soybean inhibitor (Kassell, 1970a), and avian ovomucoids and ovoinhibitors (Kassell, 1970b).

The second component is an essentially irreversible inhibitor of the probe reagent proteolytic activity which reacts with the latter substantially by a process of molecular recognition or affinity labeling of the active site of the proteinase. Thus, "One powerful tool for the study of enzyme active sites is affinity labeling. A substrate-like molecule with structural features adequate to form a complex with the enzyme under consideration similar to the enzyme-substrate complex is designed with a reactive group in its structure. Such an active site-directed reagent can then covalently modify the enzyme's active site upon binding" (Powers, 1977). Such an active site-directed reagent is often called an "active site titrant", which nomenclature will be adopted herein (cf. Fiedler et al., 1983). In the present invention the active site titrant has a molecular weight less than about 6,000 daltons such that it has access to and reacts with the probe reagent proteinase bound by the molecular filter. Examples of generally functional classes of active site titrants include organophosphorus compounds, sulphonyl fluorides, peptide halomethyl ketones, azapeptides, acylating agents, peptidyl diazomethanes, epoxysuccinyl peptides, and haloacetyl amino acids and peptides (Barrett and Salvesen, 1986). Preferred examples are chloromethyl ketone derivatives of various amino acids and peptides, typically of molecular weight less than 1,000 daltons (Powers, 1977).

The third and final component required for elimination of residual active molecular filter, and residues of the reversible and irreversible inhibitors added above, is a proteinase or set of proteinases, herein designated as a scavenger proteinase(s). This component reacts with residual active site titrant, destroys or competitively displaces the reversible inhibitor, and reacts with residual active molecular filter. An important property of the scavenger proteinase(s) in preferred embodiments is that it does not activate a zymogen subsequently employed for signal amplification.

REFERENCE EXAMPLE 1

Preparation of Fab' fragments. This reference example assumes that one has already obtained a monoclonal or polyclonal IgG which binds the analyte of interest. An aliquot of Pepsin Avidgel TM F immobilized proteinase resin is washed twice with 0.025M sodium acetate buffer, pH 4.5 (Avidgel is a registered trademark of Bioprobe International Inc., Tustin, Cal.). The IgG, at a concentration of 10 mg/ml in buffer, is purified by overnight dialysis at 4° C. against the same buffer. To 50 μl of pre-washed Pepsin Avidgel TM F is added 200 μl of the IgG solution, and the reaction tube gently shaken at room temperature for 4 hours. The digestion is quenched by adding 100 μl of 0.3M tris-HCl buffer, pH 8.2, and mixing briefly before centrifuging for 3 minutes at 2,000 rpm.

Next the supernatant is dialyzed overnight at 4° C. against 20 mM phosphate buffer, pH 7.0. It is then applied to a small immobilized protein A affinity gel column (Protein A Sepharose TM CL-4B; Sepharose is a registered trademark of Pharmacia LKB Biotechnology, Uppsala, Sweden) previously rinsed with the same buffer. The column is eluted with buffer, and fractions containing the F(ab')$_2$ fragment pooled. For immunoglobulins which do not bind to protein A, purification can be achieved by size-exclusion and/or ion-exchange chromatography (cf. Warr, 1982; Parham, 1986; Ishikawa et al., 1988).

Thereafter the F(ab')$_2$ solution is concentrated by dialysis, and reduced to the desired Fab' fragments by reaction with 2-mercaptoethylamine as described by Ishikawa et al. (1988). These fragments are now ready to couple to the selected proteinase.

Activation of Trypsin for Coupling Purposes. High-purity porcine trypsin is dissolved at a concentration of about 0.2 mM in 0.1M phosphate buffer, pH 7.0, at 30° C. Immediately a solution of CHM-NHS (see Conjugation Methods, above) in N,N-dimethylformamide (20 mg/ml, in N,N-dimethylformamide (80 mg/ml, 100-fold molar excess), pre-heated to 30° C., is added with stirring. The reaction mixture is incubated at 30° C. for 60 minutes with continuous stirring. Any precipitate formed is removed by centrifugation, and the supernatant purified by overnight dialysis using 6,000 to 8,000 molecular weight cut-off membrane in 0.1M phosphate buffer, pH 6.0 at 4° C. with one buffer change.

This crude derivitized trypsin preparation, obtained by one of the above methods, is further purified to remove inactive products of autolysis which may be present, using immobilized trypsin-inhibitor affinity chromatography according to the method of Jany et al. (1976). Briefly the extract is applied to a 20 cm column of p-aminobenzamidine-agarose (Sigma Chemical Co., St. Louis, Mo.), and unbound substances eluted with 50 mM tris-HCl buffer, pH 7.5. Further non-specifically bound substances are removed by elution with 0.8M NaCl in the same buffer. Derivitized trypsin is then recovered by elution with buffer containing 50 mM p-aminobenzamidine. Fractions containing protein are pooled and dialyzed at 4° C. against 50 mM phosphate buffer, pH 7.0, containing 5 mM p-aminobenzamidine. The reactive trypsin solution is then concentrated to 50 to 100 μM by dialysis at 0° to 4° C.

Labeling of Fab' fragment. The maleimide-trypsin solution thus obtained is incubated with the appropriate Fab' fragment (at a molar ratio of about 1.05, enzyme-to-Fab') in 0.1M phosphate buffer, pH 6.0, containing 5 mM ethylenediaminetetraacetate (EDTA) at 4° C. for 20 hours. The solution is then made 50 mM with cysteine, and allowed to sit for 4 hours to block any residual thiol-reactive groups on activated trypsin. The conjugate is purified by chromatography on Sephadex TM G 100 size-exclusion gel (Sephadex is a registered trademark of Pharmacia LKB Biotechnology, Uppsala, Sweden). Fractions containing the conjugate are identified by polyacrylamide gel electrophoresis and pooled. This solution can be used directly or further purified by affinity chromatography as described above for derivitized trypsin. The conjugate is stored at 4° C. in the presence of 0.1%W/V bovine serum albumin, about 50 mM p-aminobenzamidine, and 0.01%W/V thimerosal. For long-term storage it is advisable to dilute the conjugate solution 1:1 with glycerol (omitting thimerosal), and store at −20° C. to inhibit autolysis.

EXAMPLE 1

Homogeneous Immunoassay for Hepatitis B Virus

A 10 μl aliquot of aqueous sample having a pH of about 6.0 to 8.5 is placed in a 500 μl plastic vial, and treated with 10 μl of probe reagent conjugate solution at a concentration of about $4 \times 10^{-10}$M (diluted as required with 0.1M tris-HCl buffer, pH 8.0, containing 0.01%W/V sodium chloride). A distilled water control is similarly treated. The conjugate consists of trypsin coupled to a Fab' fragment of a polyclonal goat antibody against hepatitis B viral surface antigen "ad/ay" (International Enzymes Inc., Fallbrook, Cal.) prepared as previously described. The sample solution is allowed to stand for at least 5 minutes during which the probe binds substantially quantitatively to any antigen present.

The mixture of sample and probe reagent is then contacted with $\alpha_2$-macroglobulin ($\alpha_2$M) molecular filter immobilized on a micro-well plate.

To prepare an $\alpha_2$M plate 500 mg of human $\alpha_2$-macroglobulin (ICN Biochemicals, Cleveland, Ohio; 60% active) is dissolved in 500 μl of saline acetate buffer of the following composition (per l): sodium acetate: 6.8 g; sodium chloride: 8.8 g; adjusted to pH 5.6 with glacial acetic acid. The solution is chilled in an ice-water bath, and treated with 40.4 μl of chilled 12 mM sodium m-periodate solution in distilled water. The solution is protected from light at 0° C. for 10 minutes to selectively oxidize sialic acid residues which terminate the carbohydrate domain of $\alpha_2$M (Van Lenten and Ashwell, 1971; Bourrillon and Razafimahaleo, 1972). The reaction is ended by adding 20 μl of 5%V/V glycerol, and dialyzed overnight at 4° C. in 50 mM acetate buffer, pH 5.0.

The oxidized $\alpha_2$M is diluted 1:1 with pH 5 buffer, and 20 μl applied to about 48 wells of an Affi-Prep HZ TM derivitized micro-well plate (Bioprobe International, Inc. Tustin, Cal.). The plate, covered with cellophane, is left for 16 hours at 4° C. for reaction of hydrazide groups on the well bottoms with the aldehyde groups of oxidized $\alpha_2$M. The latter is then recovered and the wells washed six times with cold tris-buffered saline (TBS). TBS has a pH of about 7.2 and the following composition (per 1): TRIZM ™ base: 2.42 g (TRIZMA is a registered trademark of Sigma Chemical Co., St. Louis, Mo., for tris[hydroxymethly]aminomethane); 0.20N HCl: 42 ml; and sodium chloride: 29.2 g. The $\alpha_2$M activity is quite stable if the plates are stored at 4° C. with 10%W/V glycine in the wells.

To effect the molecular filtering process the following solutions are placed in order into a well of the $\alpha_2$M plate:

1) 5.0 µl of 5.0 mM sodium glycodeoxycholate in 2.0M tris-HCl buffer, pH 8.0;
2) 10 µl of sample/probe reagent solution;
3) 10 µl of trypsinogen solution, essentially freed of trypsin contamination as previously described, at a concentration of about 6.0 mg/ml in 50 mM phthalate buffer, pH 3.5.

After allowing 30 minutes for the molecular filtering process, the solution (25 µl) is transferred to a well of a standard plastic micro-well plate containing 25 µl of the following zymogen activation solution: sodium glycodeoxycholate: 7.0 mM; calcium chloride: 16 mM; in 0.64 M tris-HCl buffer, pH 8.0. Trypsinogen activation, if any, is allowed to proceed at room temperature for 20 minutes; longer incubation times can be used for increased sensitivity.

To reveal the presence of trypsin, if any, each well is treated with 25 µl of the following freshly-prepared chromogen solution: 5,5- dithiobis(2-nitrobenzoic acid): 1.1 mM; $N_\alpha$-CBZ-L-lysine thiobenzyl ester (Sigma Chemical Co., St. Louis, Mo.): 0.47 mM; in 0.2M tris-HCl buffer, pH 8.0. Strongly positive wells are indicated by development of a yellow collor within a few seconds. Alternatively the absorbance of each sample or control solution can be read after 10 to 15 minutes at 412 nm using a spectrophotometric plate reader.

EXAMPLE 2

Heterogeneous Immunoassay (ELISA) for Salmonella

This Example illustrates the operation of the invention without zymogenic amplification. All operations are at room temperature unless otherwise noted. In this embodiment 50 µl of Salmonella common structural antibody (CSA-1; Kirkegaard & Perry Laboratories, Inc., Gaithersburg, Md.) at a concentration of about 5 mg/l in 0.2M carbonate buffer, pH 9.6, is incubated for one hour in (MultiScreen is a registered trademark of Millipore Corp., Bedford, Mass.; nitrocellulose membrane, Type HATF, 0.45 µm pore size). This capture reagent solution is removed by vacuum filtration on a manifold, then 100 µl of 3%W/V bovine serum albumin in tris-buffered saline (TBS, see above) is added to each well. This 30 minute blocking step serves to occupy a high proportion of sites at which non-specific adsorption of protein occurs. The wells are then washed four times with TBS-A (TBS buffer containing 1.0 g/l bovine serum albumin). Plates so-prepared can be stored conveniently at room temperature, or preferably refrigerated.

Thereafter test samples or dilutions in TBS-A of an approximately $10^8$ cells/ml nutrient broth culture of Salmonella typhimurium (ATCC No. 13311) are applied to the wells. Specifically each well is treated with 50 µl of each sample dilution or control (each in triplicate or quadruplicate), and incubated for 30 minutes for antigen-antibody binding to occur. This process effectively immobilizes on the membrane most Salmonella cells initially present. The wells are then washed six times with TBS-A.

Probe reagent consists of bovine $\alpha$-chymotrypsin coupled to a CSA-1 Fab' fragment essentially as previously described for probe reagents incorporating trypsin. In the present case crude maleimide-derivitized chymotrypsin is reacted with the Fab' fragment without prior purification of the former. After completion of the cysteine blocking step the conjugate is dialyzed at 4° C. against several changes of 0.1M phosphate buffer, pH 6.0. It is then purified by covalent chromatography on a Thiopropyl Sepharose ™ 6B gel containing thiol groups which bind unreacted Fab' fragments (Sepharose is a registered trademark of Pharmacia LKB Biotechnology, Uppsala, Sweden). The conjugate is eluted with TBS-A containing 0.1M cysteine, and its concentration adjusted to about 10 mg/l.

Each well is treated with 50 µl of probe reagent conjugate solution at a concentration of about 10 mg/l in TBS-A. During this treatment probe reagent binds specifically to any Salmonella cells present, but also non-specifically to various surfaces. After 15 minutes the plate is drained and washed four times with TBS-A.

Thereafter follows the crucial step of reduction of the background signal, i.e. non-specifically bound probe reagent and proteinases, by application of a molecular added, having a concentration of about 10 mg/l in 0.1M phosphate buffer, pH 7.0, containing 1%W/V rehydrated bovine serum and 0.02% W/V Tween ™ 20. The molecular filtering process is continued for 10 minutes to essentially inactivate relative to the detection substrate any probe reagent not specifically bound to analyte. The plate is then drained and washed four times with TBS.

Therafter the chymotrypsin activity of the probe reagent bound to analyte is detected by the luciferase digestion method of Njus et al. (1974; cf. Worthington, 1988). Thus 50 µl of a solution of bacterial luciferase at a concentration of about 100 mg/l in 0.05M phosphate buffer, pH 7.0, containing 0.1 mM dithiothreitol is added. Proteolysis is allowed to proceed for about 20 to 30 minutes. The solution is then filtered into a 96-well collection tray, each well containing 200 µl of a solution of 0.2%W/V bovine serum albumin, 0.1 mM decanal, 0.05 mM flavin mononucleotide, and 1.6 mM reduced nicotinamide adenine dinucleotide in 20 mM phosphate buffer, pH 7.0. The peak intensity of the light signal produced is measured at 495 nm in a ML1000 microplate luminometer (Dynatech Laboratories, Inc., Chantilly, Va.), and is inversely proportional to the number of S. typhimurium cells initially present in the sample.

EXAMPLE 3

Heterogeneous Assay for Coliform Bacteria by Oligonuleotide Hybridization

This assay detects segments of the lamB gene common to E. coli, Salmonella and Shigella species (i.e. coliform bacteria) when present in very low amounts. Oligonuleotides for the required capture and probe reagents are synthesized, and the former given a homopolymer "tail" following Bej et al. (1990). Briefly, 50 mer oligonucleotide capture reagent (LB-1) is augmented at its 3'-OH end with a 400 homopolymer dT tail, and purified. This is bound to the nitrocellulose membrane of a 96-well filtration plate (see Preferred Embodiment No. 2) for 15 to 30 minutes at 50° C. as described by Jablonski et al. (1986). Plates thus prepared can be stored conveniently under humid conditions at 4° C.

Probe reagent oligonucleotide is a 24 mer region (BR-5452; Bej et al., 1990) coupled to trypsin via a modified thymine base containing a "linker arm" according to the same authors. Briefly, a protected linker arm nucleoside 3'-phosphoramidite is prepared, and incorporated directly into BR-5452 during automated nucleotide synthesis. After purification by reverse phase HPLC, the linker arm is activated by a 5 minute reaction with disuccinimidyl suberate. The reaction mixture is purified on Sephade TM G-25, and the pooled oligonucleotide fraction immediately coupled with high-purity porcine trypsin. The coupling reaction is performed at pH 8.25 for 10 hours using a two-fold trypsin excess (Jablonski et al., 1986), and in the presence of 20 mM EDTA which serves to minimize trypsin autolysis by sequestering any calcium ions present. The probe reagent conjugate is separated from unreacted oligonucleotide and autolyzed trypsin by p-aminobenzamidine-agarose affinity chromatography as previously described.

Samples possibly containing coliform bacteria are boiled for 10 minutes, then cooled on ice for 10 minutes, to break the cells and denature their DNA. Hybridization of this sample DNA to the immobilized capture reagents is performed for 20 minutes at 55° C. according to the instructions of Bej et al. (1990). Thereafter remaining active sites on the membrane are advantageously blocked for 30 minutes with 3%W/V bovine serum albumin.

Next the membranes are pre-hybridized for 10 minutes according to the procedure of Jablonski et al. (1986). Then 50 μl of probe reagent solution, at a concentration of about 5 μM in pH 7.0 citrate buffer augmented with 50 mM p-aminobenzamidine, is hybridized to bound sample DNA for 20 minutes at 50° C. (ibid.). Thereafter the membranes are washed four times with 0.15M citrate buffer, pH 7.0, containing 0.15M NaCl and 0.02 %W/V Tween TM 20, and pre-equilibrated to a temperature of 40° C.

The essential step of reduction of background signal by means of a molecular filter is performed next. Thus 75 μl of $\alpha_2$-macroglobulin solution, at a concentration of about 10 mg/l in the above buffer supplemented with %W/V rehydrated bovine serum, and 0.02%V/V Tween TM 20 is added to each membrane well and incubated for 10 minutes. During this period the molecular filter reacts with probe reagent not immobilized via analyte and the oligonucleotide capture reagent. The molecular filter solution is removed, and the wells rinsed six times with TBS-A containing 0.2%W/V fibrinogen to displace as much of the former as possible.

Thereafter the residual proteolytic activity of probe reagent bound by any adsorbed molecular filter is substantially eliminated. Thus is added 50 μl of a solution of about 50 μM $\alpha_1$-antitrypsin in TBS, and the plate incubated for about two minutes. Then 25 μl of about 3 mM TLCK in TBS is added, and the solution mixed and incubated for about 10 minutes. Next is added 200 μl of a solution of activated papain, at a concentration of about 0.75 mM in TBS containing about 15 mM EDTA, 70 mM cysteine-HCl and 85 mM 2-mercaptoethanol. The solution is mixed and incubated for about 10 minutes. This is removed by filtration, and the plate washed four times with TBS.

Enzymatic signal amplification is achieved during about 15 minutes by treatment of each well with 50 μl of a proteinase-free zymogen solution, containing about 0.175 mM trypsinogen, 1.25 mM SDS, and 1.5 mM $CaCl_2$ in 0.1M borate buffer, pH 8.0.

Thereafter signal amplification is effectively terminated and revealed by addition of 50 μl of a 2 mM solution of $N_{60}$-benzoyl-DL-arginine-$\beta$-naphthylamide in 100 mM tris-HCl buffer, pH 8.0, containing 40 mM $CaCl_2$. The plate is incubated at 37° C. for 10 minutes, then the reaction stopped by protein precipitation by addition of 200 μl of cold 95%V/V ethanol. The contents of each well are filtered into a 96-well collection tray and their fluorescence measured at 400 nm using excitation at 295 nm in a MicroFLUOR TM microplate fluorometer (MicroFLUOR is a registered trademark of Dynatech Laboratories, Inc., Chantilly, Va.).

EXAMPLE 4

Homogeneous Assay for Luteoviruses by Oligonucleotide Hybridization

This assay detects a common segment of the luteovirus coat protein gene using an oligonucleotide probe similar to that described by Robertson et al. (1991). Probe reagent is a 16 mer deoxyribonucleotide to which is coupled a commercially available thiol linker arm, the latter reacted with trypsin previously activated using a maleimide ester. This probe hybridizes in solution to complementary sequences of RNA of barley yellow dwarf virus (BYDV-PAV), beet western yellow virus (BWYV) and potato leafroll virus (PLRV).

Specifically the 16 mer oligonucleotide is 5' GCCAGTGGTTUTGGTC 3', after Robertson et al. (1991), and published genetic codes for BYDV-PAV (Miller et al., 1988), BWYV (Veidt et al., 1988), and PLRV (van der Wilk et al., 1989). It is readily prepared by automated DNA synthesis using cyanoethyl phosphoramidite chemistry. In the final synthetic cycle the 5' end of the ologonucleotide is reacted with a commercial derivitization reagent incorporating a blocked thiol group on a six-carbon linker arm ($C_6$-Thiol-Modifier TM; registered trademark of Clontech Laboratories, Inc., Palo Alto, Cal.). The modified oligonucleotide is cleaved from the resin and deprotected with silver nitrate and dithiothreitol following the manufacturer's instructions. After extraction of excess dithiothreitol with ethyl acetate the oligonucleotide is immediately coupled with maleimide-activated trypsin as previously described.

The reaction is allowed to proceed at 4° C. and pH 6.0 for 20 hours, at a molar ratio of about 1.05, enzyme-to-oligonucleotide. The solution is then made 50 mM with cysteine, and allowed to sit for 4 hours to block any residual thiol-reactive groups on activated trypsin. The conjugate is purified by affinity chromatography on p-aminobenzamidine-agarose as previously described, but eluting with 30 mM tris-HCl buffer, pH 7.6, containing 50 mM p-aminobenzamidine, 3M NaCl, 1 mM $MgCl_2$, and 0.1 mM $ZnCl_2$ (Bopp et al., 1990). The conjugate can be stored for long periods in aliquots at $-20°$ C., or for shorter periods at 4° C. in the presence of 0.05%W/V sodium azide.

Samples possibly containing luteoviruses, and diluted 1:1 V/V in 0.1M tris-HCl buffer, pH 7.6, containing 2M NaCl, 3 mM $MgCl_2$ and 0.3 mM $ZnCl_2$, are boiled for 10 minutes, then cooled on ice for an equal period, to solubilize and denature viral RNA. The above probe reagent solution (10 μl at a concentration of about 0.1 mg/ml) is added to 50 μl of the sample solution in a 500 μl conical vial, and incubated at 45° C. for 15 minutes. During this period the probe reagent hybridizes specifically to complementary sequences in viral genomic RNA if present.

The sample is then subjected to molecular filtering by means of $\alpha_2$-macroglobulin immobilized on a microwell plate as described under Preferred Embodiment No. 1.

Thereafter, in order to amplify the probe reagent signal, about 20 μl of sample solution is withdrawn from the well, and added to 100 μl of a solution containing about 0.2 mM trypsinogen, 5 mM sodium glycodeoxycholate and 25 mM $CaCl_2$ in 0.1M tris-HCl buffer, pH 8.0. The solution is incubated for about 20 minutes at room temperature.

The trypsin activity so formed, if any, is revealed by addition of 50 μl of a 15 mM solution of benzoyl-L-arginine-p-nitroanilide in 0.1M tris-HCl buffer, pH 8.0, containing 0.3M $CaCl_2$. The solution is mixed, and allowed to stand for 15 minutes, and its absorbance read at a wavelength of about 410 nm.

CONCLUSION, RAMIFICATIONS AND SCOPE OF INVENTION

Thus the reader will see that the present invention provides for fast and ultra-sensitive assay of a wide range of substances of clinical and epidemiological importance. Its application to pathogen and toxin detection is expected to significantly benefit humanity through prompt and sensitive detection and diagnosis of such noxious agents, preventing suffering and economic loss. The invention can be fruitfully applied to medical, environmental, veterinary, plant protection, forensic and other types of analyses.

The invention operates by employing a molecular filter to selectively reduce proteolytic activity not specifically bound to analyte (i.e. background noise). In preferred embodiments this discrimination process is intensified, either by use of immobilized molecular filter, or by an inventive combination of reversible and irreversible inhibitors, and scavenger proteinase. These concerted measures greatly increase the signal-to-noise ratio, most productively at low signal levels in zymogen amplified assays. Thus the detection limit by a one-hour immunoassay by this method appears to be less than 100 cells/ml, or about 100 times more sensitive than the existing limit of about $10^4$ cells/ml (Luk and Lindberg, 1991). The detection limit for DNA or RNA is less than five cells. These results compare very favourably in terms of sensitivity with PCR amplification methods employing reversible capture background reduction (Yolken et al., 1991), while avoiding the repetitive, labour-intensive, and time consuming operations of the latter.

The invention represents a simple but effective means of background reduction by use of an agent herein called a molecular filter. This device allows the performance in most cases of simple homogeneous, non-competitive assays which provide the greatest sensitivity, speed and convenience. Such a capability has heretofore largely eluded practical realization.

It will be clear to those skilled in the art that the invention is applicable to many types of assay format other than those explicitly described. Thus it can be employed in an immunoblot or dot blot type assay commonly employed for antigens or DNA respectively, wherein the sample is transferred to a solid surface (e.g. membrane) prior to detection. Alternatively it can be used for background reduction in a flow injection analysis (FIA) system, possibly prior to enzymatic signal amplification. Ultimate on-line detection can then be achieved by proteolytic formation of amino acids, and their reaction with an amino acid oxidase enzyme immobilized on an amperometric electrode.

An especially simple detection system employing the invention can likewise be produced in a "dipstick" format similar to that described by Gould and Marks (1988). Briefly the test device consists of a strip of sorbent material on which are deposited the following substances in order, each adjacent to the other: probe reagent; immobilized molecular filter; zymogen amplification mixture; and chromogen mixture. Thus as sample liquid phase is drawn up the strip by capillary forces a sequential assay occurs as follows:

i) probe reagent is dissolved and binds to any analyte present in the sample;

ii) as this solution traverses the immobilized molecular filter zone any probe reagent not bound to analyte is inactivated;

iii) as the solution traverses the amplification zone proteinase zymogen is activated by any probe reagent leaving the molecular filter zone; and, iv) as the solution enters the chromogen zone colour is produced if any substantial amount of proteinase activity is thereby present in the solution.

An advantage of this embodiment is that any residual activity of probe reagent bound by the molecular filter is without consequence since the zymogen amplification step does not occur in the presence of the molecular filter (cf. Preferred Embodiments No. 1 and No. 4).

It will be evident to those skilled in the art that the differing substrate specificities of the various proteinases susceptible to the action of molecular filters permit the simultaneous measurement in principle of more than one analyte. Thus different proteinases having mutually exclusive substrates can be coupled to different molecular recognition moieties, each specific for a particular analyte. Use of one of these specific substrates in a signal processing or detection step therefore allows the measurement of its corresponding analyte in the presence of, and possibly simultaneously with, other analytes.

The examples provided should not be construed as limitations on the scope of the invention, but rather as exemplifications of certain preferred embodiments thereof.

While the macroglobulins are the only naturally occurring "molecular filters" presently known to Applicant, other substances capable of acting as "molecular filters" of proteolytic activity may be equivalent to and substitutable for the macroglobulins, and therefore within the scope of the invention.

All references cited anywhere in this specification are hereby incorporated by reference.

REFERENCES

Aisina, R. B., Kazanskaya, N. F., and Berezin, I. V. (1975), Biol. Abstr. 59, Abstract No. 14118.

Anderson, L. E., Walsh, K. A., and Neurath, H. (1977), Biochemistry 16, 3354–3360.

Andrade, J. D., and Hlady, V. (1986), Adv. Polymer Sci. 79, 1–63.

Aoyagi, S., Kusumi, M., Matsuyuki, A., Maeda, M., and Tsuji, A. (1991), J. Immunol. Meth. 137, 73–78.

Barrett, A. J. (1981), Meth. Enzymol. 80, 737–754.

Barrett, A. J., and Starkey, P. M. (1973), Biochem. J. 133, 709–724.

Barrett, A. J., and McDonald, J. K. (1980), Mammalian Proteases: A Glossary and Bibliography, Vol. 1, Endopeptidases, Academic Press, London.

Barrett, A. J., and Salvesen, G. (1986), Eds., Proteinase Inhibitors, Elsevier Science Publishers, Amsterdam.

Bates, D. L. (1987), Trends in Biotechnol. 5, 204–209.

Bates, D. L. (1989), Ann. Biol. Clin. 47, 527–532.

Bej, A. K., Mahbubani, M. H., Miller, R., DiCesare, J. L. Haff, L., and Atlas, R. M. (1990), Mol. Cell. Probes 4, 353–365.

Bopp, C. A., Threatt, V. L., Moseley, S. L., Wells, J. G., and Wachsmuth, I. K. (1990), Mol. Cell. Probes 4, 193–203.

Bourrillon, R., and Razafimahaleo, E. (1972), pp. 699–716, in A. Gottschalk (Ed.), Glycoproteins, Part A, Elsevier, Amsterdam.

Burdon, M. G. (1980), Clin. Chim. Acta 100, 225–229.

Chan, D. W. (1987), pp. 1–23, in D. W. Chan and M. T. Perlstein (Eds.), Immunoassay: A practical guide, Academic Press, Orlando, Fla.

Cheng, S.-Y., Merlino, G. Y., and Pastan, I. H. (1983), Nucleic Acids Res. 11, 659–669.

Connolly, B. A. (1985), Nucleic Acids Res. 13, 4485–4502.

Cosstick, R., McLaughlin, L. W., and Eckstein, F. (1984), Nucleic Acids Res. 12, 1791–1810.

Durkee, K. H., Cheng, T. M., and Doellgast, G. J. (1990), Anal Biochem. 184, 375–380.

Eddowes, M. J. (1987/88), Biosensors 3, 1–15.

Ehrat, M., Cecchini, D. J., and Geise, R. W. (1986), Clin. Chem. 32, 1622–1630.

Fiedler, F., Seemuller, U., and Fritz, H. (1983), pp. 297–314, in H. U. Bergmeyer (Ed.), Methods of Enzymatic Analysis, Vol. V, 3rd ed., Verlag-Chemie, Weinheim, Germany.

Fujiwara, K., Yasuno, M., and Kitagawa, T. (1981), J. Immunol. Meth. 45, 195–203.

Gettins, P., Crews, B. C., and Cunningham, L. W. (1988), J. Cell Biol. 107 (6, Pt. 3), 835a.

Gould, B. J., and Marks, V. (1988), pp. 3–26, in T. T. Ngo (Ed.), Nonisotopic Immunoassay, Plenum Press, New York, N.Y.

Hames, B. D., and Higgins, S. J. (1985), (Eds.), Nucleic Acid Hybridisation: A Practical Approach, IRL Press, Oxford.

Harpel, P. C., and Hayes, M. B. (1980), Anal. Biochem. 108, 166–175.

Heidtmann, H., and Travis, J. (1986), pp. 441–456, in A. J. Barrett and G. Salvesen (Eds.), Proteinase Inhibitors, Elsevier, Amsterdam.

Howell, J. B., Beck, T., Bates, B., and Hunter, M. J. (1983), Arch. Biochem. Biophys. 221, 261–270.

Imagawa, M., Yoshitake, S., Hamaguchi, Y., Ishikawa, E., Niitsu, Y., Urushizaki, I., Kanazawa, R., Tachibana, S., Nakazawa, N., and Ogawa, H. (1982), J. Appl. Biochem. 4, 41–57.

Ishikawa, E., Imagawa, M., Hashida, S., Yoshitake, S., Hamaguchi, Y., and Ueno, T. (1983), J. Immunoassay 4, 209–327.

Ishikawa, E., Hashida, S., Kohno, T., and Tanaka, K. (1988), pp. 27–55, in T. T. Ngo (Ed.), Nonisotopic Immunoassay, Plenum Press, New York, N.Y.

Ishikawa, E., Hashida, S., and Kohno, T. (1991), Mol. Cell. Probes 5, 81–95.

Jablonski, E., Moomaw, E. W., Tullis, R. H., and Ruth, J. L. (1986), Nucleic Acids Res. 14, 6115–6128.

Jany, K. D., Keil, W., Meyer, H., and Kiltz, H. H. (1976), Biochim. Biophys. Acta 453, 62–66.

Kaplan, J., and Nielsen, M. L. (1979). J. Biol. Chem. 254, 7329–7335.

Kassell, B. (1970a), Meth. Enzymol. 19, 853–862.

Kassell, B. (1970b), Meth. Enzymol. 19, 890–906.

Kay, J., and Kassell, B. (1971), J. Biol. Chem. 246, 6661–6665.

Kazanskaya, N. F., Aisina, R. B., and Berezin, I. V. (1983), Enzyme Microbial Technol. 5, 209–214.

Keil, B. (1971), pp. 249–275, in P. D. Boyer (Ed.), The Enzymes, Vol. 3, 3rd ed., Academic Press, New York, N.Y.

Kennedy, K. E., Daskalakis, S. A., Davies, L., and Zwadyk, P. (1989), Mol. Cell. Probes 3, 167–177.

Kitagawa, T., Fujiwara, K., Tomonoh, S., Takahashi, K., and Koida, M. (1983), J. Biochem. 94, 1165–1172.

Kobatake, E., Nishimori, Y., Ikariyama, Y., Aizawa, M., and Kato, S. (1990), Anal. Biochem. 186, 14–18.

Kwoh, D. Y., and Kwoh, T. J. (1990), Am. Biotechnol. Lab., Oct. 1990, 14–25.

Kwok, S., and Higuchi, R. (1989), Nature 339, 237–238.

Lamoyi, E. (1986), Meth. Enzymol. 121, 652–663.

Laskowski, M., Jr., and Kato, I. (1980), Ann. Rev. Biochem. 49, 593–626.

Laurell, C.-B., and Jeppsson, J.-O. (1975), pp. 229–264, in F.W. Putnam (Ed.), The Plasma Proteins, Vol. 1, 2nd ed., Academic Press, New York.

Lazdunski, M., and Delaage, M. (1965), Biochim. Biophys. Acta 105, 541–561.

Lejeune, R., Thunus, L., Gomez, F., Frankenne, F., Cloux, J.-L., and Hennen, G. (1990), Anal. Biochem. 189, 217–222.

Liabakk, N.-B., Nustad, K., and Espevik, T. (1990), J. Immunol. Meth. 134, 253–259.

Lin, J. N., Andrade, J. D., and Chang, I.-N. (1989), J. Immunol. Meth. 125, 67–77.

Litchfield, W. J., Freytag, J. W., and Adamich, M. (1984), Clin. Chem. 30, 1441–1445.

Lizardi, P. M., and Kramer, F. R. (1991), Trends in Biotechnol. 9, 53–58.

Luk, J. M. C., and Lindberg, A. A. (1991), J. Immunol. Meth. 137, 1–8.

Mayer, M., Khassis, S., and Shafrir, E. (1974), Anal. Biochem. 58, 25–29.

Means, G. E., and Feeney, R. E. (1971), Chemical Modification of Proteins, Holden-Day, San Francisco, Cal.

Miller, W. A., Waterhouse, P. M., and Gerlach, W. L. (1988), Nucl. Acids Res. 16, 6097–6111.

Mohammad, K., and Esen, A. (1989), J. Immunol. Meth. 117, 141–145.

Moreland, B. H., and Sarkany, R. P. E. (1985), Biochem. Soc. Trans. 13, 267.

Moreland, B. H., Sarkany, R. P. E., and Wilson, R. A. (1985), ibid., 341.

Moreland, B. H., and Sanyal, K. K. (1985), ibid., 1147.

Moss, D. W., Henderson, A. R., and Kachmar, J. F. (1987), pp. 346–421, in N. W. Tietz (Ed.), Fundamentals of Clinical Chemistry, 3rd ed.,W. B. Saunders Co., Phiadelphia, Pa.

Narang, S. A. (1987), (Ed.), Synthesis and Applications of DNA and RNA, Academic Press, Orlando, Fla.

Ngo, T. T. (1985), pp. 3–32, in T. T. Ngo and H. M. Lenhoff (Eds.), Enzyme-mediated Immunoassay, Plenum Press, New York, N.Y.

Nicholls, P. J., and Malcolm, A. D. B. (1989), J. Clin. Lab. Anal. 3, 122-135.

Njus, D., Baldwin, T. O., and Hastings, J. W. (1974), Anal. Biochem. 61, 280-287.

Parham, P., Androlewicz, M. J., Brodsky, F. M., Holmes, N.J., and Ways, J. P. (1982), J. Immunol. Meth. 53, 133-173.

Parham, P. (1986), Ch. 14, in D. M. Weir (Ed.), Handbook of Experimental Immunology, Vol. 1, Immunochemistry, 4th ed., Blackwell Scientific Publications, Oxford.

Pechère, J.-F., and Neurath, H. (1957), J. Biol. Chem. 229, 389-407.

Powers, J. C. (1977), pp. 65-178, in B. Weinstein (Ed.), Chemistry and Biochemistry of Amino Acids, Peptides, and Proteins, Vol. 4, Marcel Dekker, New York.

Pruslin, F. H., To, S. E., Winston, R., and Rodman, T. C. (1991), J. Immunol. Meth. 137, 27-35.

Renz, M., and Kurz, C. (1984), Nucleic Acids Res. 12, 3435-3444.

Rinderknecht, H., and Geokas, M. C. (1973), Biochim. Biophys. Acta 295, 233-244.

Robertson, N. L., French, R., and Gray, S. M. (1991), J. Gen. Virol. 72, 1473-1477.

Rose, S. D. (1990), Am. Biotechnol. Lab., Oct. 1990, 31-33.

Rousseaux, J., Rousseaux-Prevost, R., and Bazin, H. (1986), Meth. Enzymol. 121, 663-669.

Ruth, J. L., Morgan, C., and Pasko, A. (1985), DNA 4, 93.

Ruth, J. L., and Jablonski, E. (1987), Nucleosides & Nucleotides 6, 541-542.

Sarkany, R. P. E., and Moreland, B. H. (1985), Biochim. Biophys. Acta 839, 262-267.

Shaw, E., Mares-Guia, M., and Cohen, W. (1965), Biochemistry 4, 2219-2224.

Sproat, B. S., Beijer, B., Rider, P., and Neuner, P. (1987), Nucleic Acids Res. 15, 4837-4848.

Sproat, B. S., Beijer, B., Rider, P., and Neuner, P. (1988), Nucleosides & Nucleotides 7, 651-653.

Starkey, P. M., and Barrett, A. J. (1977), pp. 663-696, in A. J. Barrett (Ed.), Proteinases in Mammalian Cells and Tissues, North-Holland, Amsterdam.

Stenberg, M., and Nygren, H. (1988), J. Immunol. Meth. 113, 3-15.

Syvanen, A.-C., Laaksonen, M., and Soderlund, H. (1986), Nucleic Acids Res. 14, 5037-5048.

Tijssen, P. (1985), Practice and Theory of Enzyme Immunoassays, Elsevier Science Publishers, Amsterdam.

Travis, J., and Salvesen, G. S. (1983), Ann. Rev. Biochem. 52, 655-709.

Urdea, M. S., Running, J. A., Horn, T., Clyne, J., Ku, L., and Warner, B. D. (1987), Gene 61, 253-264.

van der Wilk, F., Huisman, M. J., Cornelissen, B. J. C., Huttinga, H., and Goldbach, R. (1989), FEBS Lett. 245, 51-56.

Van Lenten, L., and Ashwell, G. (1971), J. Biol. Chem. 246, 1889-1894.

Van Leuven, F., Cassiman, J.-J., and Van Den Berghe, H. (1979), J. Biol. Chem. 254, 5155-5160.

Van Leuven, F., Cassiman, J.-J., and Van Den Berghe, H. (1981), J. Biol. Chem. 256, 9016-9022.

Veidt, I., Lot, H., Leiser, M., Scheidecker, D., Guilley, H., Richards, K., and Jonard, G. (1988), Nucl. Acids Res. 16, 9917-9932.

Walsh, K. A. (1970), Meth. Enzymol. 19, 41-63.

Warr, G. W. (1982), pp. 59-96, in J. J. Marchalonis and G. W. Warr (Eds.), Antibody as a Tool, John Wiley and Sons, Chichester, England.

Wilkinson, P. C. (1988), Meth. Enzymol. 162, 180-192.

Worthington, C. C. (1988), Ed., Worthington Enzyme Manual, Worthington Biochemical Corp., Freehold, N.J.

Yolken, R. H., Sierra-Honigmann, A. M., and Viscidi, R. P. (1991), Mol. Cell. Probes 5, 151-156.

Yoshitake, S., Yamada, Y., Ishikawa, E., and Masseyeff, R. (1979), Eur. J. Biochem. 101, 395-399.

Yoshitake, S., Imagawa, M., Ishikawa, E., Niitsu, Y., Urushizaki, I., Nishiura, M., Kanazawa, R., Kurosaki, H., Tachibana, S., Nakazawa, N., and Ogawa, H. (1982), J. Biochem. 92, 1413-1424.

What I claim is:

1. In a method of detecting or quantifying an analyte in a sample in which the sample is incubated with
   (i) a noncompetitive probe reagent comprising a conjugate of an analyte binding molecule (ABM) and a label, or
   (ii) an analyte binding molecule, and a competitive probe reagent comprising a conjugate of an analyte analogue and a label, to form a mixture, the sample analyte interacting with said ABM to form an analyte:ABM complex in said mixture, and a signal is simultaneously or subsequently generated which is indicative of the presence or amount of sample analyte in said complex, the improvement comprising:
   (a) said label being selected from the group consisting of proteinases and proteinase precursors, the proteinase essentially retaining its proteolytic activity after said reagent binds to sample analyte to form said complex, said signal being generated directly or indirectly as the result of the action of said proteinase on a substrate, and the label, if a proteinase precursor, being converted to such a proteinase prior to signal generation, and
   (b) incubating with said mixture an alpha macroglobulin which is capable of modifying said proteinase in uncomplexed probe reagent so as to reduce its proteolytic activity on said substrate to a detectably greater degree than it so modifies said proteinase in complexed probe reagent
   wherein the total molecular weight of said probe reagent is not greater than about 90,000 daltons, and the molecular weight of the substrate is at least about 10,000 daltons,
   and wherein, when the method of detection or quantification is a non-competitive homogeneous assay, in which a probe reagent-analyte complex is formed, the total molecular weight of the probe reagent-analyte complex is at least about 95,000 daltons.

2. The method of claim 1 wherein the alpha macroglobulin essentially does not reduce the proteolytic activity of the proteinase in complexed probe reagent.

3. The method of claim 2 wherein the alpha macroglobulin essentially abolishes the proteolytic activity of the proteinase in uncomplexed probe reagent with regard to said substrate.

4. The method of claim 1 wherein the alpha macroglobulin is alpha$_2$ macroglobulin.

5. The method of claim 1 wherein said improvement achieves a substantial reduction of background interference and an increase in the signal-to-noise ratio prior to signal processing or detection.

6. The method of claim 1 wherein the method is a competitive, homogeneous assay.

7. The method of claim 1 wherein the method is a non-competitive homogeneous assay.

8. The method of claim 1 wherein the method is a competitive, heterogeneous assay.

9. The method of claim 1 wherein the method is a non-competitive heterogeneous assay.

10. The method of claim 1 wherein the analyte is an antigen and the probe reagent is a specifically binding fragment of an antibody.

11. The method of claim 1 wherein the analyte is an oligonucleotide or polynucleotide and the probe reagent is an oligonucleotide or polynucleotide sufficiently complementary with the analyte to specifically hybridize thereto.

12. The method of claim 1 wherein the analyte comprises a carbohydrate moiety and the probe reagent is a lectin which binds specifically to said moiety.

13. The method of claim 1 wherein the proteinase is selected from the group consisting of chymotrypsin, trypsin, thrombin, plasmin, plasma kallikrein, acrosin, pancreatic elastase, cathepsin G, leukocyte elastase, arvin, batroxobin, cercarial proteinase of *Schistosoma mansonii*, brinase, Serratia spp. E15proteinase, *Staphylococcus aureus* "acid" proteinase, *Staphylococcus aureus* V8 proteinase, subtilisins A and B, cathepsin B, cathepsin H, cathepsin L, calcium-dependent proteinase, papain, ficin, bromelain, clostripain, chymosin, cathepsin D, periplaneta acid proteinase, vertegrate non-leukocyte collagenases, leukocyte collagenases, *Crotalus atrox* venom proteinase, *Crotalus adamanteus* venom proteinase, *Trichophyton mentagraphytes* keratinase, *Pseudomonas aeruginosa* elastase, thermolysi, *Bacillus subtilis* metalloproteinase, *Proteus vulgaris* neutral proteinase and *Fusiformis nodosus* neutral proteinase.

14. The method of claim 1 wherein the proteinase is a trypsin or a proteolytically active fragment or derivative thereof.

15. The method of claim 1 wherein residual biochemical activities from operation of a macroglobulin are substantially eliminated by incubating said mixture, prior to signal generation, with, in order:

i) a reversible active site-specific inhibitor of said proteinase, said inhibitor interacting specifically with probe reagent not trapped by the macroglobulin in an amount sufficient to protect said untrapped probe reagent from the action of (ii) below;

ii) an effectively irreversible, active site-specific inhibitor of said proteinase, in an amount sufficient to inhibit all proteinase not protected by said reversible inhibitor and thereby to substantially eliminate any residual proteolytic activity still associated with uncomplexed probe reagent trapped by said macroglobulin;

and then displacing, removing or inactivating said reversible inhibitor and any excess irreversible inhibitor, whereby said previously protected probe reagent may participate in signal generation.

16. The method of claim 15 wherein the reversible inhibitor is $\alpha_1$-antiproteinase or $\alpha_1$-antitrypsin.

17. The method of claim 15 wherein the active site-specific irreversible inhibitor is a halomethyl ketone.

18. The method of claim 15 wherein the reversible inhibitor is a peptide or protein and is inactivated with activated papain.

19. The method of claim in which both uncompleted macroglobulin and macroglobulin which has entrapped probe reagent are separated from said mixture prior to signal generation.

20. The method of claim 19 in which the macroglobulin is immobilized on a support.

21. The method of claim 19 in which the macroglobulin is removed by binding it to an immobilized anti-macroglobulin reagent.

22. The method of claim 1 in which the substrate is a zymogen, said proteinase acting on said substrate to generate a second enzyme which in turn acts upon a second substrate, thereby directly or indirectly generating said signal.

23. The method of claim 22 in which the proteinase is trypsin and the substrate is N$\alpha$-CBZ-L-Lysine thiobenzyl ester.

* * * * *